United States Patent [19]

Hardies et al.

[11] 4,150,226

[45] Apr. 17, 1979

[54] 1-(3-ALKYL, OR ALKARYL, 4-H, OR ALKYL, OR ARYL-5-ISOTHIAZOLYL)-2-OXO-3-(ALKYL, ALKENYL, OR ALKYNYL)-5-(ALKYL, ALKENYL, OR ALKYNYL) HEXAHYDRO-1,3,5-TRIAZINES

[75] Inventors: Donald E. Hardies, Wadsworth; Dennis K. Krass, Canal Fulton, both of Ohio

[73] Assignee: PPG Industries, Inc., Pittsburgh, Pa.

[21] Appl. No.: 876,583

[22] Filed: Feb. 9, 1978

[51] Int. Cl.$^2$ .................................................. C07D 251/08
[52] U.S. Cl. ........................................ 544/220; 71/90
[58] Field of Search ........................................ 544/220

[56]  References Cited

U.S. PATENT DOCUMENTS

| | | | |
|---|---|---|---|
| 3,563,985 | 2/1971 | Volpp et al. | 260/247.1 |
| 3,696,101 | 10/1972 | Litt et al. | 260/248 NS |
| 3,705,155 | 12/1972 | Miller | 260/248 NS |
| 3,849,412 | 11/1974 | Krenzer | 260/248 NS |
| 3,860,593 | 1/1975 | Krenzer | 260/248 NS |
| 4,020,065 | 4/1977 | Rathgeb | 544/220 |

FOREIGN PATENT DOCUMENTS 1045412  10/1966  United Kingdom.

OTHER PUBLICATIONS

Clemens, et al., J. of Org. Chem., vol, 26, pp. 767–769 (1961).

*Primary Examiner*—John M. Ford
*Attorney, Agent, or Firm*—Robert J. Grassi

[57] ABSTRACT

Disclosed are compositions of 1-(3-alkyl, or 3-alkaryl, 4-H, or 4-alkyl or 4-aryl-5-isothiazolyl)-2-oxo-3-(alkyl, or alkenyl, or alkynyl)-5-(alkyl, alkenyl, or alkynyl)hexahydro-1,3,5-triazines such as 1-(3-methyl-5-isothiazolyl)-2-oxo-3-methyl-5-isopropylhexahydro-1,3,5-triazine which are useful for controlling weeds, as well as the control of weeds with the compounds.

132 Claims, No Drawings

1-(3-ALKYL, OR ALKARYL, 4-H, OR ALKYL, OR ARYL-5-ISOTHIAZOLYL)-2-OXO-3-(ALKYL, ALKENYL, OR ALKYNYL)-5-(ALKYL, ALKENYL, OR ALKYNYL) HEXAHYDRO-1,3,5-TRIAZINES

BACKGROUND OF THE INVENTION

1. Field of the Invention

The invention relates to 1-(isothiazolyl)-2-oxo-hexahydro-1,3,5-triazines, particularly 1-(substituted isothiazolyl)-2-oxo-3-(substituted)-5-(substituted)hexahydro-1,3,5-triazines; for example 1-(3-methyl-5-isothiazolyl)-2-oxo-3-methyl-5-isopropylhexahydro-1,3,5-triazine and their use in controlling weeds.

2. Description of the Prior Art

The chemical compositions and control of undesirable plants (weeds) described herein is neither suggested or taught in the prior art. The prior art concerns itself with processes of making the triazines or forming thiadiazole-triazine type compositions. For example, U.S. Pat. No. 3,563,985 discloses the formation of isothiazoles having an urea, carbamate, or thiocarbamate attached to the 3 or 5 position of the isothiazole ring. U.S. Pat. No. 3,860,593 discloses substituted thiadiazoles-substituted triazines such as 1-(5-isopropyl-1,3,4-thiadiazol-2-yl)-2-oxo-3-methyl-5-benzylhexahydro-1,3,5-triazine. U.S. Pat. No. 3,849,412 discloses substituted 1-thiadiazol-substituted hexahydro-1,3,5-triazines, such as 1-(5-isopropyl-1,3,4-thiadiazol-2-yl)-2-oxo-3,5-dimethylhexahydro-1,3,5-triazine. U.S. Pat. No. 3,705,155 discloses substituted 1-thiadiazolyl-2-oxo-substitutedhexahydro-1,3,5-triazine such as 1-(1,2,4-triadiazol-5-yl)-2-oxo-3,5-dimethylhexahydro-1,3,5-triazine.

U.S. Pat. No. 3,696,101 discloses substituted 2-tetrahydrobenzothiazolyl-substituted hexahydro-1,3,5-triazines, such as 1-(2-[5,5,7-trimethyl]-4,5,6,7-tetrahydrobenzothiazolyl)-2-oxo-3,5-dimethylhexahydro-1,3,5-triazine.

D. H. Clemens et al, *Journal of Organic Chemistry*, 26, pages 767-769, 1961, describes the reactions of isocyanates and isothiocyanates with azomethines to form triazones and thiatriazones.

SUMMARY OF THE INVENTION

Novel compositions useful for controlling weeds are disclosed which have the following general formulas:

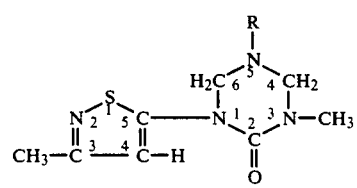

wherein:
R is a lower alkyl of from two to four carbon atoms, a lower alkenyl of from three to five carbon atoms with a saturated carbon atom attached to the nitrogen atom, or a lower alkynyl of from three to five carbon atoms with a saturated carbon atom attached to the nitrogen atom; and

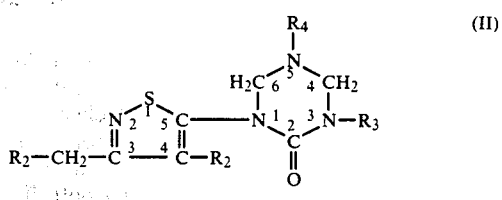

wherein:
$R_2$ is methyl, ethyl, n-propyl, phenyl, p-chlorophenyl, or p-nitrophenyl; and $R_3$ and $R_4$ may together or independently be a lower alkyl of from one to four carbon atoms, a lower alkenyl of from three to five carbon atoms with a saturated carbon atom attached to the nitrogen atom, or a lower alkynyl of from three to five carbon atoms with a saturated carbon atom attached to the nitrogen atom; but $R_3$ and $R_4$ can not both be methyl.

The invention also concerns the use of the compositions of general formulas I or II to control weeds, specific compounds represented by the general formulas are:

1-(3-methyl-5-isothiazolyl)-2-oxo-3-methyl-5-ethylhexahydro-1,3,5-triazine;
1-(3-methyl-5-isothiazolyl)-2-oxo-3-ethyl-5-methylhexahydro-1,3,5-triazine; and
1-(3-ethyl-4-methyl-5-isothiazolyl)-2-oxo-3,5-dimethylhexahydro-1,3,5-triazine.

DETAILED DESCRIPTION OF THE INVENTION

The novel agriculturally useful compositions of this invention for controlling weeds are represented by the following general formulas:

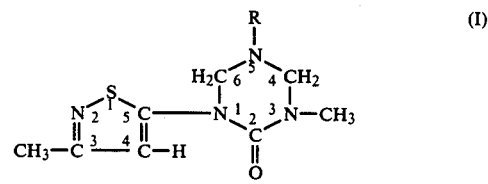

wherein:
R is a lower alkyl of from two to four carbon atoms, a lower alkenyl of from three to five carbon atoms with a saturated carbon atom attached to the nitrogen atom or a lower alkynyl of from three to five carbon atoms with a saturated carbon atom attached to the nitrogen atom; and

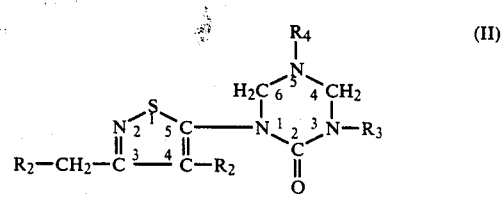

wherein:
$R_2$ is methyl, ethyl, n-propyl, phenyl, p-chlorophenyl, or p-nitrophenyl;
$R_3$ is a lower alkyl of from one to four carbon atoms, a lower alkenyl of from three to five carbon atoms with a saturated carbon atom attached to the nitrogen atom, or a lower alkynyl of from three to five carbon atoms with a saturated carbon atom attached to the nitrogen atom; and R$_4$ is a lower alkyl of from one to four carbon atoms, a lower alkenyl of from three to five carbon atoms with a saturated carbon atom attached to the nitrogen atom, or a lower alkynyl of from three to five carbon atoms with a saturated carbon atom attached to the nitrogen atom; but both R$_3$ and R$_4$ can not be methyl.

The phrase, "a lower alkyl from one to four carbon atoms" as used herein and in the claims, refers to methyl, ethyl, n-propyl, isopropyl, n-butyl, sec-butyl, isobutyl, and t-butyl. The phrase, "a lower alkyl of from two to four carbon atoms" as used herein and in the claims, refers to ethyl, n-propyl, isopropyl, n-butyl, isobutyl, sec-butyl, and t-butyl.

The phrase, "a lower alkenyl of from three to five carbon atoms with a saturated carbon atom attached to the nitrogen atom" as used herein and in the claims, refers to:

allyl (—CH$_2$ — CH = CH$_2$),
2-butenyl (—CH$_2$ — CH = CH — CH$_3$),
2-methyl-2-propenyl (—CH$_2$ — C(CH$_3$) = CH$_2$),
1-methyl-2-propenyl (—CH(CH$_3$) — CH = CH$_2$),
3-butenyl (—CH$_2$ — CH$_2$ — CH = CH$_2$),
2-pentenyl (—CH$_2$ — CH = CH — CH$_2$CH$_3$),
1-methyl-2-butenyl (—CH(CH$_3$) — CH = CH — CH$_3$),
1,1-dimethyl-2-propenyl (—C(CH$_3$)$_2$ — CH = CH$_2$),
3-methyl-2-butenyl (—CH$_2$ — CH = C(CH$_3$) — CH$_3$),
2-methyl-2-butenyl (—CH$_2$ — C(CH$_3$) = CH — CH$_3$),
3-pentenyl (—CH$_2$ — CH$_2$ — CH = CH — CH$_3$),
3-methyl-3-butenyl (—CH$_2$ — CH$_2$ — C(CH$_3$) = CH$_2$),
2-methyl-3-butenyl (—CH$_2$ — CH(CH$_3$) — CH = CH$_2$),
1-methyl-3-butenyl (—CH(CH$_3$) — CH$_2$ — CH = CH$_2$), and
4-pentenyl (—CH$_2$ — CH$_2$ — CH$_2$ — CH = CH$_2$).

The phrase, "a lower alkynyl of from three to five carbon atoms with a saturated carbon atom attached to the nitrogen atom" refers to:

2-propynyl (—CH$_2$ — C ≡ CH),
2-butynyl (—CH$_2$ — C ≡ C — CH$_3$),
1-methyl-2-propynyl (—CH(CH$_3$) — C ≡ CH),
3-butynyl (—CH$_2$ — CH$_2$ — C ≡ CH),
2-pentynyl (—CH$_2$ — C ≡ C — CH$_2$ — CH$_3$),
1-methyl-2-butynyl (—CH(CH$_3$) — C ≡ C — CH$_3$),
1,1-dimethyl-2-propynyl (—C(CH$_3$)$_2$ — C ≡ CH),
3-pentynyl (—CH$_2$ — CH$_2$ — C ≡ C — CH$_3$),
1-methyl-3-butynyl (—CH(CH$_3$) — CH$_2$ — C ≡ CH),
2-methyl-3-butynyl (—CH$_2$ — CH(CH$_3$) — C ≡ CH), and
4-pentynyl (—CH$_2$ — CH$_2$ — CH$_2$ — C ≡ CH).

Representative compounds of general formula (I) are:
 1-(3-methyl-5-isothiazolyl)-2-oxo-3-methyl-(5-sec-butyl)hexahydro-1,3,5-triazine;
 1-(3-methyl-5-isothiazolyl)-2-oxo-3-methyl-5-(4-pentenyl)hexahydro-1,3,5-triazine; and
 1-(3-methyl-5-isothiazolyl)-2-oxo-3-methyl-5-(4-pentynyl)hexahydro-1,3,5-triazine.

The compounds of the general formula (I) which are most useful are those in which R is a lower alkyl from two to four carbon atoms. Highly useful are the compounds where R is a lower alkyl of from two to four carbon atoms are:
 1-(3-methyl-5-isothiazolyl)-2-oxo-3-methyl-5-ethylhexahydro-1,3,5-triazine;
 1-(3-methyl-5-isothiazolyl)-2-oxo-3-methyl-5-n-propylhexahydro-1,3,5-triazine;
 1-(3-methyl-5-isothiazolyl)-2-oxo-3-methyl-5-isopropylhexahydro-1,3,5-triazine; and
 1-(3-methyl-5-isothiazolyl)-2-oxo-3-methyl-5-t-butylhexahydro-1,3,5-triazine.

The compounds of general formula (I) wherein R is a lower alkenyl of from three to five carbon atoms with a saturated carbon atom attached to the nitrogen atom are very useful. Of these compounds, those compounds in which R is an alkenyl consisting of allyl, 2-butenyl, 3-butenyl, or 2-methyl-2-propenyl are particularly useful, especially 1-(3-methyl-5-isothiazolyl)-2-oxo-3-methyl-5-allylhexahydro-1,3,5-triazine and 1-(3-methyl-5-isothiazolyl)-2-oxo-3-methyl-5-(2-methyl-2-propenyl)hexahydro-1,3,5-triazine.

Those compounds of general formula (I) in which R is a lower alkynyl of from three to five carbon atoms with a saturated carbon atom attached to the nitrogen atom are also very useful in controlling weeds, especially those in which R is an alkynyl of 2-propynyl, 1,1-dimethylpropynyl, 2-butynyl, and 3-butynyl, particularly 1-(3-methyl-5-isothiazolyl)-2-oxo-3-methyl-5-(2-propynyl)hexahydro-1,3,5-triazine and 1-(3-methyl-5-isothiazolyl)-2-oxo-3-methyl-5-(1,1-dimethyl-2-propynyl)hexahydro-1,3,5-triazine.

Specific examples representative of the useful compositions of general formual (II) are:
 1-(3-p-nitrobenzyl-4-p-nitrophenyl-5-isothiazolyl)-2-oxo-3-t-butyl-5-t-butylhexahydro-1,3,5-triazine;
 1-(3-p-nitrobenzyl-4-p-nitrophenyl-5-isothiazolyl)-2-oxo-3-(4-pentenyl)-5-t-butylhexahydro-1,3,5-triazine;
 1-(3-p-nitrobenzyl-4-p-nitrophenyl-5-isothiazolyl)-2-oxo-3-(4-pentynyl)-5-t-butylhexahydro-1,3,5-triazine;
 1-(3-p-nitrobenzyl-4-p-nitrophenyl-5-isothiazolyl)-2-oxo-3-t-butyl-5-(3-pentenyl)hexahydro-1,3,5-triazine;
 1-(3-p-nitrobenzyl-4-p-nitrophenyl-5-isothiazolyl)-2-oxo-3-t-butyl-5-(3-pentynyl)hexahydro-1,3,5-triazine;
 1-(3-p-nitrobenzyl-4-p-nitrophenyl-5-isothiazolyl)-2-oxo-3-(4-pentenyl)-5-(4-pentenyl)hexahydro-1,3,5-triazine;
 1-(3-p-nitrobenzyl-4-p-nitrophenyl-5-isothiazolyl)-2-oxo-3-(4-pentenyl)-5-(4-pentynyl)hexahydro-1,3,5-triazine;
 1-(3-p-nitrobenzyl-4-p-nitrophenyl-5-isothiazolyl)-2-oxo-3-(4-pentynyl)-5-(4-pentynyl)hexahydro-1,3,5-triazine;
 1-(3-benzyl-4-phenyl-5-isothiazolyl)-2-oxo-3-isobutyl-5-iso-butylhexahydro-1,3,5-triazine;
 1-(3-benzyl-4-phenyl-5-isothiazolyl)-2-oxo-3-isobutyl-5-(1-methyl-3-butenyl)hexahydro-1,3,5-triazine;
 1-(3-benzyl-4-phenyl-5-isothiazolyl)-2-oxo-3-isobutyl-5-(2-methyl-3-butynyl)hexahydro-1,3,5-triazine;
 1-(3-benzyl-4-phenyl-5-isothiazolyl)-2-oxo-3-(1-methyl-3-butenyl)-5-isobutylhexahydro-1,3,5-triazine;
 1-(3-benzyl-4-phenyl-5-isothiazolyl)-2-oxo-3-(2-methyl-3-butynyl)-5-isobutylhexahydro-1,3,5-triazine;

1-(3-benzyl-4-phenyl-5-isothiazolyl)-2-oxo-3-(1-methyl-3-butenyl)-5-(1-methyl-3-butenyl)hexahydro-1,3,5-triazine;
1-(3-benzyl-4-phenyl-5-isothiazolyl)-2-oxo-3-(1-methyl-3-butenyl)-5-(2-methyl-3-butynyl)hexahydro-1,3,5-triazine;
1-(3-benzyl-4-phenyl-5-isothiazolyl)-2-oxo-3-(2-methyl-3-butynyl)-5-(2-methyl-3-butynyl)hexahydro-1,3,5-triazine;
1-(3-n-butyl-4-n-propyl-5-isothiazolyl)-2-oxo-3-n-butyl-5-n-butylhexahydro-1,3,5-triazine;
1-(3-n-butyl-4-n-propyl-5-isothiazolyl)-2-oxo-3-n-butyl-5-(2-methyl-3-butenyl)hexahydro-1,3,5-triazine;
1-(3-n-butyl-4-n-propyl-5-isothiazolyl)-2-oxo-3-n-butyl-5-(1-methyl-3-butynyl)hexahydro-1,3,5-triazine;
1-(3-n-butyl-4-n-propyl-5-isothiazolyl)-2-oxo-3-(2-methyl-3-butenyl)-5-n-butylhexahydro-1,3,5-triazine;
1-(3-n-butyl-4-n-propyl-5-isothiazolyl)-2-oxo-3-(2-methyl-3-butenyl)-5-(1-methyl-3-butynyl)hexahydro-1,3,5-triazine;
1-(3-n-butyl-4-n-propyl-5-isothiazolyl)-2-oxo-3-(2-methyl-3-butenyl)-5-(2-methyl-3-butenyl)hexahydro-1,3,5-triazine;
1-(3-n-butyl-4-n-propyl-5-isothiazolyl)-2-oxo-3-(1-methyl-3-butynyl)-5-n-butylhexahydro-1,3,5-triazine;
1-(3-n-butyl-4-n-propyl-5-isothiazolyl)-2-oxo-3-(1-methyl-3-butynyl)-5-(2-methyl-3-butenyl)hexahydro-1,3,5-triazine;
1-(3-n-butyl-4-n-propyl-5-isothiazolyl)-2-oxo-3-(1-methyl-3-butynyl)-5-(1-methyl-3-butynyl)hexahydro-1,3,5-triazine;
1-(3-n-propyl-4-ethyl-5-isothiazolyl)-2-oxo-3-isopropyl-5-isopropylhexahydro-1,3,5-triazine;
1-(3-n-propyl-4-ethyl-5-isothiazolyl)-2-oxo-3-isopropyl-5-(3-methyl-3-butenyl)hexahydro-1,3,5-triazine;
1-(3-n-propyl-4-ethyl-5-isothiazolyl)-2-oxo-3-isopropyl-5-(1-methyl-2-butynyl)hexahydro-1,3,5-triazine;
1-(3-n-propyl-4-ethyl-5-isothiazolyl)-2-oxo-3-(3-methyl-3-butenyl)-5-isopropylhexahydro-1,3,5-triazine;
1-(3-n-propyl-4-ethyl-5-isothiazolyl)-2-oxo-3-(3-methyl-3-butenyl)-5-(3-methyl-3-butenyl)hexahydro-1,3,5-triazine;
1-(3-n-propyl-4-ethyl-5-isothiazolyl)-2-oxo-3-(3-methyl-3-butenyl)-5-(1-methyl-2-butynyl)hexahydro-1,3,5-triazine;
1-(3-n-propyl-4-ethyl-5-isothiazolyl)-2-oxo-3-(1-methyl-2-butynyl)-5-isopropylhexahydro-1,3,5-triazine;
1-(3-n-propyl-4-ethyl-5-isothiazolyl)-2-oxo-3-(1-methyl-2-butynyl)-5-(3-methyl-3-butenyl)hexahydro-1,3,5-triazine;
1-(3-n-propyl-4-ethyl-5-isothiazolyl)-2-oxo-3-(1-methyl-2-butynyl)-5-(1-methyl-2-butynyl)hexahydro-1,3,5-triazine;
1-(3-ethyl-4-methyl-5-isothiazolyl)-2-oxo-3-t-butyl-5-isopropylhexahydro-1,3,5-triazine;
1-(3-ethyl-4-methyl-5-isothiazolyl)-2-oxo-3-t-butyl-5-(3-pentenyl)hexahydro-1,3,5-triazine;
1-(3-ethyl-4-methyl-5-isothiazolyl)-2-oxo-3-t-butyl-5-(2-pentynyl)hexahydro-1,3,5-triazine;
1-(3-ethyl-4-methyl-5-isothiazolyl)-2-oxo-3-(3-pentenyl)-5-t-butylhexahydro-1,3,5-triazine;
1-(3-ethyl-4-methyl-5-isothiazolyl)-2-oxo-3-(3-pentenyl)-5-(3-pentenyl)hexahydro-1,3,5-triazine;
1-(3-ethyl-4-methyl-5-isothiazolyl)-2-oxo-3-(3-pentenyl)-5-(2-pentynyl)hexahydro-1,3,5-triazine;
1-(3-ethyl-4-methyl-5-isothiazolyl)-2-oxo-3-(2-pentynyl)-5-t-butylhexahydro-1,3,5-triazine;
1-(3-ethyl-4-methyl-5-isothiazolyl)-2-oxo-3-(2-pentynyl)-5-(3-pentenyl)hexahydro-1,3,5-triazine; and
1-(3-ethyl-4-methyl-5-isothiazolyl)-2-oxo-3-(2-pentynyl)-5-(2-pentynyl)hexahydro-1,3,5-triazine.

Those compositions of general formula (II) in which $R_2$ is methyl are very useful, especially when $R_3$ is a lower alkyl selected from the group consisting of methyl, isopropyl, or t-butyl, and especially preferred are those in which $R_4$ is a lower alkyl selected from the group consisting of methyl, ethyl, isopropyl, or t-butyl, but both $R_3$ and $R_4$ cannot be methyl.

The compositions of general formula (II), wherein $R_2$ is methyl, $R_3$ is a lower alkyl of methyl, isopropyl, or t-butyl, and $R_4$ is a lower alkenyl of from three to five carbon atoms with a saturated carbon atom attached to the nitrogen atom are useful, particularly when $R_4$ is a lower alkenyl of allyl, 2-butenyl, 3-butenyl, or 2-methyl-2-propenyl.

The compositions of general formula (II), wherein $R_2$ is methyl, $R_3$ is a lower alkyl of methyl, isopropyl, or t-butyl, and $R_4$ is a lower alkynyl of from three to five carbon atoms with a saturated carbon atom attached to the nitrogen atom are very useful, particularly when $R_4$ is a lower alkynyl of 2-propynyl, 2-butynyl, 3-butynyl, or 1,1-dimethyl-2-propynyl.

Specific examples representative of the compositions of general formula (II), wherein $R_2$ is methyl and $R_3$ is methyl, isopropyl, or t-butyl, and $R_4$ is methyl, but not when $R_3$ is methyl, ethyl, isopropyl, or t-butyl, or is a lower alkenyl of from three to five carbon atoms with a saturated carbon atom attached to the nitrogen atom or $R_4$ is a lower alkynyl of from three to five carbon atoms with a saturated carbon atom attached to the nitrogen atom are:

1-(3-ethyl-4-methyl-5-isothiazolyl)-2-oxo-3-methyl-5-isobutylhexahydro-1,3,5-triazine;
1-(3-ethyl-4-methyl-5-isothiazolyl)-2-oxo-3-ethyl-5-(4-pentenyl) hexahydro-1,3,5-triazine;
1-(3-ethyl-4-methyl-5-isothiazolyl)-2-oxo-3-sec-butyl-5-(4-pentynyl)hexahydro-1,3,5-triazine;
1-(3-ethyl-4-methyl-5-isothiazolyl)-2-oxo-3-methyl-5-isopropylhexahydro-1,3,5-triazine;
1-(3-ethyl-4-methyl-5-isothiazolyl)-2-oxo-3-methyl-5-t-butylhexahydro-1,3,5-triazine;
1-(3-ethyl-4-methyl-5-isothiazolyl)-2-oxo-3-isopropyl-5-methylhexahydro-1,3,5-triazine;
1-(3-ethyl-4-methyl-5-isothiazolyl)-2-oxo-3,5-diisopropylhexahydro-1,3,5-triazine;
1-(3-ethyl-4-methyl-5-isothiazolyl)-2-oxo-3-isopropyl-5-t-butylhexahydro-1,3,5-triazine;
1-(3-ethyl-4-methyl-5-isothiazolyl)-2-oxo-3-t-butyl-5-methylhexahydro-1,3,5-triazine;
1-(3-ethyl-4-methyl-5-isothiazolyl)-2-oxo-3-t-butyl-5-isopropylhexahydro-1,3,5-triazine;
1-(3-ethyl-4-methyl-5-isothiazolyl)-2-oxo-3,5-di-t-butylhexahydro-1,3,5-triazine;
1-(3-ethyl-4-methyl-5-isothiazolyl)-2-oxo-3-methyl-5-(4-pentenyl)hexahydro-1,3,5-triazine;
1-(3-ethyl-4-methyl-5-isothiazolyl)-2-oxo-3-methyl-5-(2-methyl-2-butenyl)hexahydro-1,3,5-triazine;

1-(3-ethyl-4-methyl-5-isothiazolyl)-2-oxo-3-methyl-5-allylhexahydro-1,3,5-triazine;

1-(3-ethyl-4-methyl-5-isothiazolyl)-2-oxo-3-methyl-5-(2-butenyl)hexahydro-1,3,5-triazine;

1-(3-ethyl-4-methyl-5-isothiazolyl)-2-oxo-3-methyl-5-(3-butenyl)hexahydro-1,3,5-triazine;

1-(3-ethyl-4-methyl-5-isothiazolyl)-2-oxo-3-methyl-5-(2-methyl-2-propenyl)hexahydro-1,3,5-triazine;

1-(3-ethyl-4-methyl-5-isothiazolyl)-2-oxo-3-methyl-5-(1-methyl-3-butynyl)hexahydro-1,3,5-triazine;

1-(3-ethyl-4-methyl-5-isothiazolyl)-2-oxo-3-methyl-5-(2-pentynyl)hexahydro-1,3,5-triazine;

1-(3-ethyl-4-methyl-5-isothiazolyl)-2-oxo-3-methyl-5-(2-propynyl)hexahydro-1,3,5-triazine;

1-(3-ethyl-4-methyl-5-isothiazolyl)-2-oxo-3-methyl-5-(2-butynyl)hexahydro-1,3,5-triazine;

1-(3-ethyl-4-methyl-5-isothiazolyl)-2-oxo-3-methyl-5-(3-butynyl)hexahydro-1,3,5-triazine;

1-(3-ethyl-4-methyl-5-isothiazolyl)-2-oxo-3-methyl-5-(1,1-dimethyl-2-propynyl)hexahydro-1,3,5-triazine;

1-(3-ethyl-4-methyl-5-isothiazolyl)-2-oxo-3-isopropyl-5-sec-butylhexahydro-1,3,5-triazine;

1-(3-ethyl-4-methyl-5-isothiazolyl)-2-oxo-3-isopropyl-5-(2-pentenyl)hexahydro-1,3,5-triazine;

1-(3-ethyl-4-methyl-5-isothiazolyl)-2-oxo-3-isopropyl-5-allylhexahydro-1,3,5-triazine;

1-(3-ethyl-4-methyl-5-isothiazolyl)-2-oxo-3-isopropyl-5-(2-butenyl)hexahydro-1,3,5-triazine;

1-(3-ethyl-4-methyl-5-isothiazolyl)-2-oxo-3-isopropyl-5-(3-butenyl)hexahydro-1,3,5-triazine;

1-(3-ethyl-4-methyl-5-isothiazolyl)-2-oxo-3-isopropyl-5-(2-methyl-2-propenyl)hexahydro-1,3,5-triazine;

1-(3-ethyl-4-methyl-5-isothiazolyl)-2-oxo-3-isopropyl-5-(1-methyl-2-propynyl)hexahydro-1,3,5-triazine;

1-(3-ethyl-4-methyl-5-isothiazolyl)-2-oxo-3-isopropyl-5-(2-propynyl)hexahydro-1,3,5-triazine;

1-(3-ethyl-4-methyl-5-isothiazolyl)-2-oxo-3-isopropyl-5-(2-butynyl)hexahydro-1,3,5-triazine;

1-(3-ethyl-4-methyl-5-isothiazolyl)-2-oxo-3-isopropyl-5-(3-butynyl)hexahydro-1,3,5-triazine;

1-(3-ethyl-4-methyl-5-isothiazolyl)-2-oxo-3-isopropyl-5-(1,1-dimethyl-2-propynyl)hexahydro-1,3,5-triazine;

1-(3-ethyl-4-methyl-5-isothiazolyl)-2-oxo-3-t-butyl-5-propylhexahydro-1,3,5-triazine;

1-(3-ethyl-4-methyl-5-isothiazolyl)-2-oxo-3-t-butyl-5-(1,1-dimethylpropenyl)hexahydro-1,3,5-triazine;

1-(3-ethyl-4-methyl-5-isothiazolyl)-2-oxo-3-t-butyl-5-allylhexahydro-1,3,5-triazine;

1-(3-ethyl-4-methyl-5-isothiazolyl)-2-oxo-3-t-butyl-5-(2-butenyl)hexahydro-1,3,5-triazine;

1-(3-ethyl-4-methyl-5-isothiazolyl)-2-oxo-3-t-butyl-5-(3-butenyl)hexahydro-1,3,5-triazine;

1-(3-ethyl-4-methyl-5-isothiazolyl)-2-oxo-3-t-butyl-5-(2-methyl-2-propenyl)hexahydro-1,3,5-triazine;

1-(3-ethyl-4-methyl-5-isothiazolyl)-2-oxo-3-t-butyl-5-(1-methyl-2-butynyl)hexahydro-1,3,5-triazine;

1-(3-ethyl-4-methyl-5-isothiazolyl)-2-oxo-3-t-butyl-5-(2-propynyl)hexahydro-1,3,5-triazine;

1-(3-ethyl-4-methyl-5-isothiazolyl)-2-oxo-3-t-butyl-5-(2-butynyl)hexahydro-1,3,5-triazine;

1-(3-ethyl-4-methyl-5-isothiazolyl)-2-oxo-3-t-butyl-5-(3-butynyl)hexahydro-1,3,5-triazine; and 1-(3-ethyl-4-methyl-5-isothiazolyl)-2-oxo-3-t-butyl-5-(1,1-dimethyl-2-propynyl)hexahydro-1,3,5-triazine.

The preferred compounds of general formula (II) in which $R_2$ is methyl, and $R_3$ is a lower alkyl, are those in which $R_3$ is methyl, particularly when $R_4$ is a lower alkyl of ethyl, or isopropyl, or a lower alkenyl of from three to five carbon atoms with a saturated carbon atom attached to the nitrogen atom, especially allyl, 2-butenyl, 3-butenyl, or 2-methyl-2-propenyl, or $R_4$ is a lower alkynyl of from three to five carbon atoms with a saturated carbon atom attached to the nitrogen atom, particularly 2-propynyl, 2-butynyl, 3-butynyl, or 1,1-dimethylpropynyl. The following compositions are especially preferred:

1-(3-ethyl-4-methyl-5-isothiazolyl)-2-oxo-3-methyl-5-ethylhexahydro-1,3,5-triazine;

1-(3-ethyl-4-methyl-5-isothiazolyl)-2-oxo-3-methyl-5-isopropylhexahydro-1,3,5-triazine;

1-(3-ethyl-4-methyl-5-isothiazolyl)-2-oxo-3-methyl-5-t-butylhexahydro-1,3,5-triazine;

1-(3-ethyl-4-methyl-5-isothiazolyl)-2-oxo-3-methyl-5-allylhexahydro-1,3,5-triazine;

1-(3-ethyl-4-methyl-5-isothiazolyl)-2-oxo-3-methyl-5-(2-methyl-2-propenyl)hexahydro-1,3,5-triazine;

1-(3-ethyl-4-methyl-5-isothiazolyl)-2-oxo-3-methyl-5-(2-propynyl)hexahydro-1,3,5-triazine; and 1-(3-ethyl-4-methyl-5-isothiazolyl)-2-oxo-3-methyl-5-(1,1-dimethyl-2-propynyl)hexahydro-1,3,5-triazine.

Those compositions of general formula (II), wherein $R_2$ is methyl and $R_3$ is a lower alkenyl of from 3 to 5 carbon atoms with a saturated carbon atom attached to the nitrogen atom, and $R_4$ is a lower alkyl or lower alkenyl or lower alkynyl as mentioned herein, are very useful.

Specific compounds representative of these compositions are as follows:

1-(3-ethyl-4-methyl-5-isothiazolyl)-2-oxo-3-(4-pentenyl-5-isobutyl)hexahydro-1,3,5-triazine;

1-(3-ethyl-4-methyl-5-isothiazolyl)-2-oxo-3-(1-methyl-3-butenyl)-5-sec-butylhexahydro-1,3,5-triazine;

1-(3-ethyl-4-methyl-5-isothiazolyl)-2-oxo-3-(3-pentenyl)-5-n-propylhexahydro-1,3,5-triazine;

1-(3-ethyl-4-methyl-5-isothiazolyl)-2-oxo-3-(1,1-dimethyl-2-propenyl)-5-n-butylhexahydro-1,3,5-triazine;

1-(3-ethyl-4-methyl-5-isothiazolyl)-2-oxo-3-(2-methyl-3-butenyl)-5-allylhexahydro-1,3,5-triazine;

1-(3-ethyl-4-methyl-5-isothiazolyl)-2-oxo-3-(2-methyl-2-butenyl)-5-(1-methyl-2-propenyl)hexahydro-1,3,5-triazine;

1-(3-ethyl-4-methyl-5-isothiazolyl)-2-oxo-3-(3-methyl-2-butenyl)-5-(2-pentenyl)hexahydro-1,3,5-triazine;

1-(3-ethyl-4-methyl-5-isothiazolyl)-2-oxo-3-(1-methyl-2-butenyl)-5-(2-methyl-3-butynyl)hexahydro-1,3,5-triazine;

1-(3-ethyl-4-methyl-5-isothiazolyl)-2-oxo-3-(1-methyl-3-butenyl)-5-(1-methyl-3-butynyl)hexahydro-1,3,5-triazine; and 1-(3-ethyl-4-methyl-5-isothiazolyl)-2-oxo-3-(2-pentenyl)-5-(1-methyl-2-butynyl)hexahydro-1,3,5-triazine.

Those compositions of general formula II, wherein $R_2$ is methyl and $R_3$ is a lower alkenyl of allyl, 2-butenyl, 3-butenyl, or 2-methyl-2-propenyl are highly useful. Particularly preferred are those in which $R_4$ is a lower alkyl of from one to four carbon atoms, particularly methyl, ethyl, n-propyl, isopropyl, or t-butyl.

Specific compounds representative of these preferred compositions are:

1-(3-ethyl-4-methyl-5-isothiazolyl)-2-oxo-3-(2-butenyl)-5-methylhexahydro-1,3,5-triazine;
1-(3-ethyl-4-methyl-5-isothaizolyl)-2-oxo-3-(3-butenyl)-5-ethylhexahydro-1,3,5-triazine;
1-(3-ethyl-4-methyl-5-isothiazolyl)-2-oxo-3-(2-butenyl)-5-t-butylhexahydro-1,3,5-triazine;
1-(3-ethyl-4-methyl-5-isothiazolyl)-2-oxo-3-(2-butenyl)-5-ethylhexahydro-1,3,5-triazine;
1-(3-ethyl-4-methyl-5-isothiazolyl)-2-oxo-3-(3-butenyl)-5-methylhexahydro-1,3,5-triazine; and
1-(3-ethyl-4-methyl-5-isothiazolyl)-2-oxo-3-(3-butenyl)-5-isopropylhexahydro-1,3,5-triazine.

Those compositions of general formula II, wherein $R_2$ is methyl, $R_3$ is a lower alkenyl of allyl, 2-butenyl, 3-butenyl, or 2-methyl-2-propenyl, and $R_4$ is a lower alkyl and are highly preferred. Specific compounds representative of these preferred compositions are:

1-(3-ethyl-4-methyl-5-isothiazolyl)-2-oxo-3-allyl-5-methylhexahydro-1,3,5-triazine;
1-(3-ethyl-4-methyl-5-isothiazolyl)-2-oxo-3-allyl-5-ethylhexahydro-1,3,5-triazine;
1-(3-ethyl-4-methyl-5-isothiazolyl)-2-oxo-3-allyl-5-isopropylhexahydro-1,3,5-triazine;
1-(3-ethyl-4-methyl-5-isothiazolyl)-2-oxo-3-allyl-5-t-butylhexahydro-1,3,5-triazine;
1-(3-ethyl-4-methyl-5-isothiazolyl)-2-oxo-3-(2-methyl-2-propenyl)-5-methylhexahydro-1,3,5-triazine;
1-(3-ethyl-4-methyl-5-isothiazolyl)-2-oxo-3-(2-methyl-2-propenyl)-5-ethylhexahydro-1,3,5-triazine;
1-(3-ethyl-4-methyl-5-isothiazolyl)-2-oxo-3-(2-methyl-2-propenyl)-5-isopropylhexahydro-1,3,5-triazine; and
1-(3-ethyl-4-methyl-5-isothiazolyl)-2-oxo-3-(2-methyl-2-propenyl)-5-(t-butyl)hexahydro-1,3,5-triazine.

Highly useful are the compositions of general formula II, in which $R_2$ is methyl and $R_3$ is an alkenyl of allyl, 2-butylene, 3-butylene, or 2-methyl-2-propylene, and in which $R_4$ is a lower alkylene of from three to five carbon atoms with a saturated carbon atom attached to the nitrogen atom as mentioned herein. Of these, the preferred compositions are those in which the alkenyl is allyl, 2-butenyl, 3-butenyl, or 2-methyl-2-propenyl.

Specific compounds representative of these compositions are:

1-(3-ethyl-4-methyl-5-isothiazolyl)-2-oxo-3-(2-butenyl)-5-(3-butenyl)hexahydro-1,3,5-triazine;
1-(3-ethyl-4-methyl-5-isothiazolyl)-2-oxo-3-(2-butenyl)-5-(4-pentenyl)hexahydro-1,3,5-triazine;
1-(3-ethyl-4-methyl-5-isothiazolyl)-2-oxo-3-(3-butenyl)-5-(2-butenyl)hexahydro-1,3,5-triazine;
1-(3-ethyl-4-methyl-5-isothiazolyl)-2-oxo-3-(3-butenyl)-5-(2-methyl-3-butenyl)hexahydro-1,3,5-triazine;
1-(3-ethyl-4-methyl-5-isothiazolyl)-2-oxo-3-allyl-3-(3-methyl-3-butenyl)hexahydro-1,3,5-triazine;
1-(3-ethyl-4-methyl-5-isothiazolyl)-2-oxo-3-allyl-5-(2-methyl-2-butenyl)hexahydro-1,3,5-triazine;
1-(3-ethyl-4-methyl-5-isothiazolyl)-2-oxo-3-allyl-5-(1-methyl-2-butenyl)hexahydro-1,3,5-triazine;
1-(3-ethyl-4-methyl-5-isothiazolyl)-2-oxo-3-(2-methyl-2-propenyl)-5-(1-methyl-3-butenyl)hexahydro-1,3,5-triazine;
1-(3-ethyl-4-methyl-5-isothiazolyl)-2-oxo-3-(2-methyl-2-propenyl)-5-(3-pentenyl)hexahydro-1,3,5-triazine;
1-(3-ethyl-4-methyl-5-isothiazolyl)-2-oxo-3-(2-butenyl)-5-(2-methyl-2-propenyl)hexahydro-1,3,5-triazine; and
1-(3-ethyl-4-methyl-5-isothiazolyl)-2-oxo-3-(2-methyl-2-propenyl)-5-(2-butenyl)hexahydro-1,3,5-triazine.

The preferred compositions of general formula II, wherein $R_2$ is methyl, and $R_3$ and $R_4$ are an alkenyl or allyl, 2-butenyl, 3-butenyl, or 2-methyl-2-propenyl are:

1-(3-ethyl-4-methyl-5-isothiazolyl)-2-oxo-3,5-diallyl-hexahydro-1,3,5-triazine;
1-(3-ethyl-4-methyl-5-isothiazolyl)-2-oxo-3-allyl-5-(2-methyl-2-propenyl)hexahydro-1,3,5-triazine;
1-(3-ethyl-4-methyl-5-isothiazolyl)-2-oxo-3,5-bis(2-methyl-2-propenyl)hexahydro-1,3,5-triazine; and
1-(3-ethyl-4-methyl-5-isothiazolyl)-2-oxo-3-(2-methyl-2-propenyl)-5-allylhexahydro-1,3,5-triazine.

Compositions of general formula II, wherein $R_2$ is methyl, $R_3$ is allyl, 2-butenyl, 3-butenyl, or 2-methyl-2-propenyl, and $R_4$ is a lower alkynyl of from three to five carbon atoms with a saturated carbon atom attached to the nitrogen atom are particularly useful, especially when $R_4$ is an alkynyl of 2-propynyl, 2-butynyl, 3-butynyl, or 1,1-dimethyl-2-propynyl. Representative compounds being:

1-(3-ethyl-4-methyl-5-isothiazolyl)-2-oxo-3-(3-butenyl)-5-(2-butynyl)hexahydro-1,3,5-triazine;
1-(3-ethyl-4-methyl-5-isothiazolyl)-2-oxo-3-(2-butenyl)-5-(3-butynyl)hexahydro-1,3,5-triazine;
1-(3-ethyl-4-methyl-5-isothiazolyl)-2-oxo-3-(2-methyl-2-propenyl)-5-(3-butynyl)hexahydro-1,3,5-triazine; and
1-(3-ethyl-4-methyl-5-isothiazolyl)-2-oxo-3-allyl-5-(2-butynyl)hexahydro-1,3,5-triazine.

The following compounds of general formula II, wherein $R_2$ is methyl, $R_3$ is allyl, 2-methyl-2-propenyl, 2-butenyl, or 3-butenyl, and $R_4$ is 2-propynyl, 2-butynyl, 3-butynyl, or 1,1-dimethyl-2-propynyl are most preferred. Representative compounds being:

1-(3-ethyl-4-methyl-5-isothiazolyl)-2-oxo-3-allyl-5-(2-propynyl)hexahydro-1,3,5-triazine;
1-(3-ethyl-4-methyl-5-isothiazolyl)-2-oxo-3-allyl-5-(1,1-dimethyl-2-propynyl)hexahydro-1,3,5-triazine;
1-(3-ethyl-4-methyl-5-isothiazolyl)-2-oxo-3-(2-methyl-2-propenyl)-5-(2-propynyl)hexahydro-1,3,5-triazine; and
1-(3-ethyl-4-methyl-5-isothiazolyl)-2-oxo-3-(2-methyl-2-propenyl)-5-(1,1-dimethyl-2-propynyl)hexahydro-1,3,5-triazine.

Those compositions of general formula II, in which $R_2$ is methyl, $R_3$ is a lower alkynyl of from three to five carbon atoms having a saturated carbon atom attached to the nitrogen ring, are particularly useful, preferably when $R_3$ is 2-propynyl, 2-butynyl, 3-butynyl, or 1,1-dimethyl-2-propynyl; and much preferred are those in which $R_4$ is a lower alkyl of from one to four carbon atoms, particularly when $R_4$ is methyl, ethyl, isopropyl, or t-butyl. The following compositions are especially preferred:

1-(3-ethyl-4-methyl-5-isothiazolyl)-2-oxo-3(2-propynyl)-5-methylhexahydro-1,3,5-triazine;
1-(3-ethyl-4-methyl-5-isothiazolyl)-2-oxo-3-(2-propynyl)-5-ethylhexahydro-1,3,5-triazine;

1-(3-ethyl-4-methyl-5-isothiazolyl)-2-oxo-3-(2-propynyl)-5-isopropylhexahydro-1,3,5-triazine;

1-(3-ethyl-4-methyl-5-isothiazolyl)-2-oxo-3-(2-propynyl)-5-(t-butyl)hexahydro-1,3,5-triazine;

1-(3-ethyl-4-methyl-5-isothiazolyl)-2-oxo-3-(1,1-dimethyl-2-propynyl)-5-methylhexahydro-1,3,5-triazine;

1-(3-ethyl-4-methyl-5-isothiazolyl)-2-oxo-3-(1,1-dimethyl-2-propynyl)-5-ethylhexahydro-1,3,5-triazine;

1-(3-ethyl-4-methyl-5-isothiazolyl)-2-oxo-3(1,1-dimethyl-2-propynyl)-5-isopropylhexahydro-1,3,5-triazine; and 1-(3-ethyl-4-methyl-5-isothiazolyl)-2-oxo-3-(1,1-dimethyl-2-propynyl)-5-(t-butyl)hexahydro-1,3,5-triazine.

Those compositions of general formula II, which $R_2$ is methyl and $R_3$ is one of the lower alkynyl mentioned herein, and $R_4$ is one of the lower alkenyls mentioned herein, are very useful, particularly those in which $R_4$ is allyl, 2-butenyl, 3-butenyl, or 2-methyl-2-propenyl, and of those the following compositions are especially preferred:

1-(3-ethyl-4-methyl-5-isothiazolyl)-2-oxo-3-(2-propynyl)-5-allylhexahydro-1,3,5-triazine;

1-(3-ethyl-4-methyl-5-isothiazolyl)-2-oxo-3-(2-propynyl)-5-(2-methyl-2-propenyl)hexahydro-1,3,5-triazine;

1-(3-ethyl-4-methyl-5-isothiazolyl)-2-oxo-3-(1,1-dimethyl-2-propynyl)-5-allylhexahydro-1,3,5-triazine; and 1-(3-ethyl-4-methyl-5-isothiazolyl)-2-oxo-3-(1,1-dimethyl-2-propynyl)-5-(2-methyl-2-propenyl)hexahydro-1,3,5-triazine.

Those compositions of general formula II, in which $R_2$ is methyl and both $R_3$ and $R_4$ are one of the lower alkynyls mentioned herein, are extremely useful; those in which $R_4$ is 2-propynyl, 2-butynyl, 3-butynyl, or 1,1-dimethyl-2-propynyl are preferred, especially when $R_4$ is 2-propynyl or 1,1-dimethyl-2-propynyl. Highly preferred are those compositions in which $R_2$ is methyl, $R_3$ is 2-propynyl, 2-butynyl, 3-butynyl, or 1,1-dimethyl-2-propynyl, especially when $R_4$ is 2-propynyl, or 1,1-dimethyl-2-propynyl with the following compositions being greatly preferred:

1-(3-ethyl-4-methyl-5-isothiazolyl)-2-oxo-3,5-bis-(2-propynyl)hexahydro-1,3,5-triazine;

1-(3-ethyl-4-methyl-5-isothiazolyl)-2-oxo-3-(2-propynyl)-5-(1,1-dimethyl-2-propynyl)hexahydro-1,3,5-triazine;

1-(3-ethyl-4-methyl-5-isothiazolyl)-2-oxo-3-(1,1-dimethyl-2-propynyl)-5-(2-propynyl)hexahydro-1,3,5-triazine; and 1-(3-ethyl-4-methyl-5-isothiazolyl)-2-oxo-3,5-bis-(1,1-dimethyl-2-propynyl)hexahydro-1,3,5-triazine.

Those compositions of general formula II are also very useful in which $R_2$ is ethyl, particularly where $R_3$ is methyl and $R_4$ is a lower alkyl of isopropyl or t-butyl; also preferred are those in which $R_4$ is a lower alkenyl of allyl, 2-methyl-2-propenyl, 2-butenyl, and 3-butenyl, as well as those in which $R_4$ is a lower alkynyl or 2-propynyl, 2-butynyl, 3-butynyl, or 1,1-dimethyl-2-propynyl; particularly preferred are:

1-(3-n-propyl-4-ethyl-5-isothiazolyl)-2-oxo-3-methyl-5-allylhexahydro-1,3,5-triazine;

1-(3-n-propyl-4-ethyl-5-isothiazolyl)-2-oxo-3-methyl-5-(2-methyl-2-propenyl)hexahydro-1,3,5-triazine;

1-(3-n-propyl-4-ethyl-5-isothiazolyl)-2-oxo-3-methyl-5-(2-propynyl)hexahydro-1,3,5-triazine; and 1-(3-n-propyl-4-ethyl-5-isothiazolyl)-2-oxo-3-methyl-5-(1,1-dimethyl-2-propynyl)hexahydro-1,3,5-triazine.

Those compositions of general formula II, wherein $R_2$ is ethyl and $R_3$ is a lower alkenyl of allyl or 2-methyl-2-propenyl are very useful, especially those in which $R_4$ is a lower alkyl of methyl, isopropyl, or t-butyl, or $R_4$ is a lower alkenyl or allyl or 2-methyl-2-propenyl, or $R_4$ is a lower alkynyl of 2-propynyl or 1,1-dimethyl-2-propynyl.

The compositions of general formula II, wherein $R_2$ is ethyl and $R_3$ is a lower alkynyl of 2-propynyl or 1,1-dimethyl-2-propynyl are very useful, especially when $R_4$ is a lower alkyl of methyl, isopropyl, or t-butyl, or a lower alkenyl of allyl, or 2-methyl-2-propenyl, or a lower alkynyl of 2-propynyl or 1,1-dimethyl-2-propynyl.

Those compositions of general formula II, are highly useful wherein $R_2$ is p-chlorophenyl and $R_3$ is methyl, particularly those compositions wherein $R_4$ is a lower alkyl of methyl, isopropyl, t-butyl, or $R_4$ is a lower alkenyl of allyl or 2-methyl-2-propenyl, or when $R_4$ is a lower alkynyl of 2-propynyl or 1,1-dimethyl-2-propynyl.

Also, the compositions of general formula II, in which $R_2$ is p-chlorophenyl and $R_3$ is a lower alkenyl of allyl or 2-methyl-2-propenyl are very useful, particularly when $R_4$ is a lower alkyl of methyl, isopropyl, or t-butyl, or $R_4$ is a lower alkenyl of allyl or 2-methyl-2-propenyl, or $R_4$ is a lower alkynyl of 2-propynyl or 1,1-dimethyl-2-propynyl.

Furthermore, the compositions of general formula II are particularly useful in which $R_2$ is p-chlorophenyl and $R_3$ is a lower alkynyl of 2-propynyl, or 1,1-dimethyl-2-propynyl, preferably when $R_4$ is a lower alkyl of methyl, isopropyl, or t-butyl, or a lower alkenyl of allyl or 2-methyl-2-propenyl, or a lower alkynyl of 2-propynyl or 1,1-dimethyl-2-propynyl.

Also, especially useful are the compositions of general formula II, in which $R_2$ is p-nitrophenyl, particularly those in which $R_3$ is methyl and especially those in which $R_4$ is a lower alkyl of isopropyl, or t-butyl, or $R_4$ is a lower alkenyl of allyl, or 2-methyl-2-propenyl, or $R_4$ is a lower alkynyl of 2-propynyl or 1,1-dimethyl-2-propynyl; those in which $R_3$ is a lower alkenyl of allyl or 2-methyl-2-propenyl, and especially those in which $R_4$ is a lower alkyl of methyl, isopropyl, or t-butyl, or $R_4$ is a lower alkenyl of allyl, or 2-methyl-2-propenyl, or $R_4$ is a lower alkynyl of 2-propynyl or 1,1-dimethyl-2-propynyl, and those in which $R_3$ is a lower alkynyl of 2-propynyl or 1,1-dimethyl-2-propynyl, especially when $R_4$ is a lower alkyl of methyl, isopropyl, or t-butyl, or a lower alkenyl of allyl, or 2-methyl-2-propenyl, or $R_4$ is a lower alkynyl of 2-propynyl or 1,1-dimethyl-2-propynyl.

SYNTHESIS OF THE COMPOSITIONS a. Synthesis of Compositions Represented by General Formula (I)

The intermediate 5-amino-3-methyl-isothiazole (III) for making the compositions of general formula (I), is generally synthesized by reaction A, according to the procedure of U.S. Pat. No. 2,871,243. Note that the reaction may yield a tautomeric mixture of the two isomers IV and V.

Reaction (A)

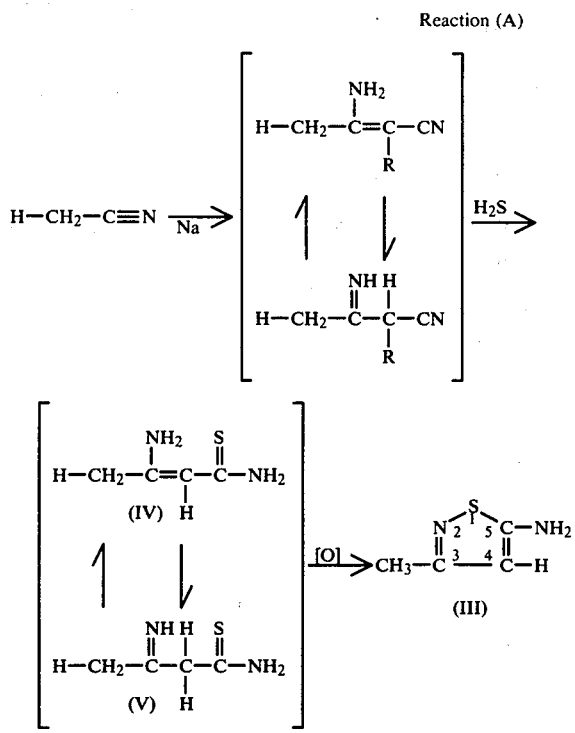

The 5-amino-3-methyliosthiazole (III) is then reacted with the methyl isocyanate (CH₃NCO) to form the corresponding urea (VI) as shown by reaction B (described in U.S. Pat. No. 3,454,591).

Reaction (B)

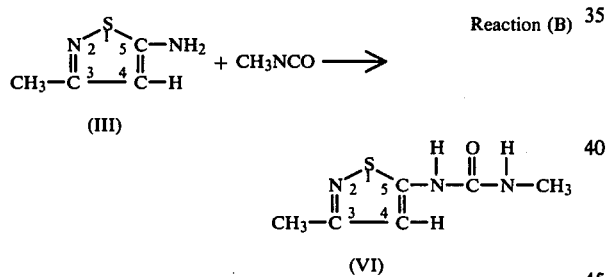

Alternatively, an isocyanate can be prepared from the 5-aminoisothiazole which in turn can be reacted with an amine to form the desired urea.

The urea (VI) is then reacted with formaldehyde and the appropriate alkyl, alkylene, or alkynyl amine (RNH₂ — wherein R has the meaning mentioned herein before) according to reaction C, to form a composition represented by general formula (I).

Reaction (C)

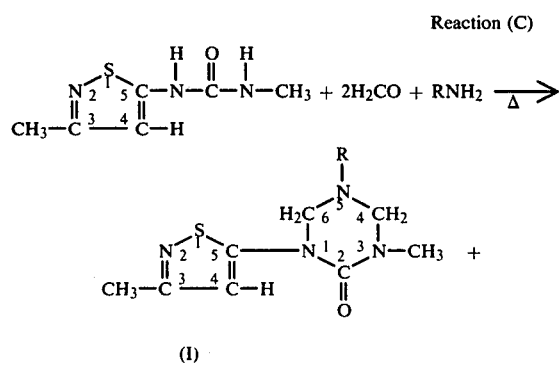

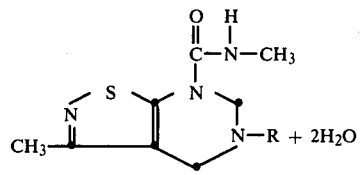

b. Synthesis of Compounds Represented by General Formula (II)

The intermediate 5-aminoisothiazoles of general formula (VII) are generally synthesized by reaction D, according to the procedure of U.S. Pat. No. 2,871,243, where R₂ is as defined herein. Note that reaction D may give a mixture of tautomeric isomers VIII and IX. In some cases these intermediates may readily hydrolyze and are best isolated as a salt which in turn is neutralized before oxidation to the corresponding substituted 5-aminoisothiazole (VII).

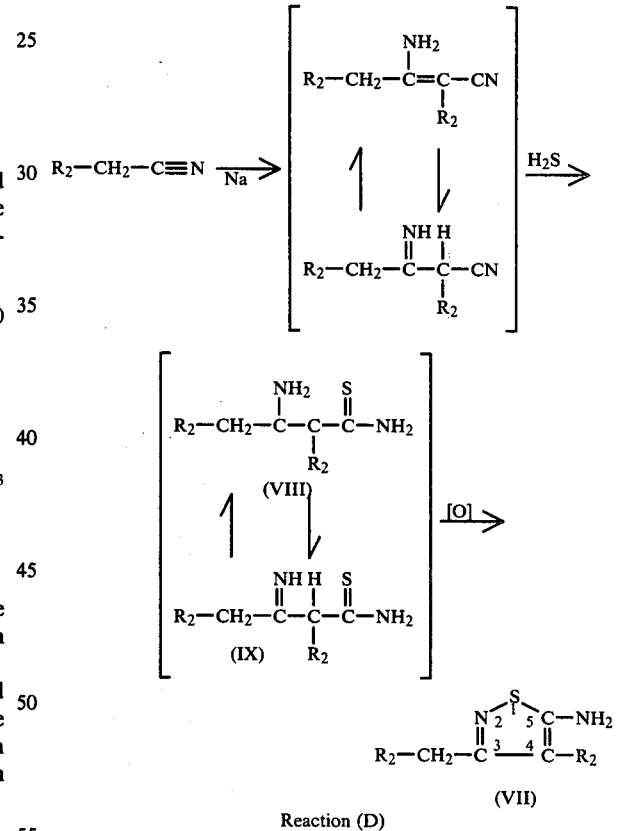

Reaction (D)

The substituted aminoisothiazoles of general formula VII are then reacted with the appropriate alkyl, alkylene, or alkynyl isocyanate of the general formula (R₃—NCO) in which R₃ has the same meaning as described herein to form the corresponding urea of general formula X, in which R₃ has the meaning as described herein, by reaction E.

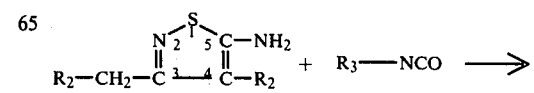

-continued

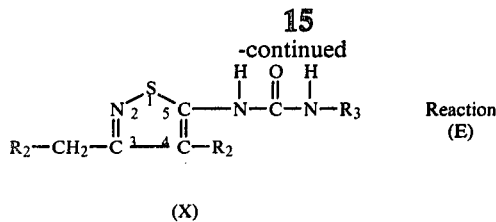

(X)

Alternatively, an isocyanate can be prepared from the appropriate substituted 5-aminoisothiazole which in turn can be reacted with an appropriate amine to form the desired urea of the general formula X.

The urea of general formula X is then reacted with formaldehyde and the appropriate alkyl, alkenyl, or alkynyl amine having the general formula ($R_4$—$NH_2$) in which $R_4$ has the same meaning as described herein according to reaction F, to form a composition represented by general formula II.

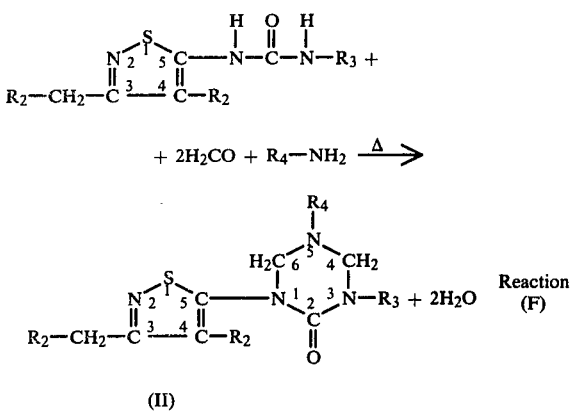

The following examples illustrate the synthesis of the compounds of this invention.

EXAMPLE 1 a. Synthesis of 1-(3-Methyl-5-isothiazolyl)-3-methylurea

5-Amino-3-methylisothiazole was obtained from its hydrochloride salt by treating the hydrochloride salt with 1N NaOH solution and extracting with ether.

The procedure described in U.S. Pat. No. 3,454,591 was followed.

Methylisocyanate (1.96 milliliters, 0.04 mole) was added dropwise to a thirty (30) milliliter solution of tetrahydrofuran (distilled from calcium hydride) containing the above mentioned 5-amino-3-methylisothiazole (5.0 grams, 0.04 mole), and then the resulting yellow solution was refluxed for 3 hours, during which time a white precipitate formed. The solution was cooled and filtered, giving 3.73 grams of 1-(3-methyl-5-isothiazolyl)-3-methylurea, also referred to as 3-methyl-5-N-methylureidoisothiazole.

b. Synthesis of 1-(3-Methyl-5-isothiazolyl)-2-oxo-3-methyl-5-ethylhexahydro-1,3,5-triazine The synthesized 1-(3-methyl-5-isothiazolyl)-3-methylurea (4.34 grams, 0.025 mole) was added to a 100 milliliter round bottom flask containing (8) milliliters of (37%) aqueous formaldehyde and (25) milliliters of dimethylformamide (DMF). The solution was stirred during the addition and then for an additional 30 to 45 minutes. (70%) aqueous ethyl amine (0.035 mole, 3.2 milliliters) was added dropwise to the stirred solution over a period of 5 to 40 minutes and the stirring was continued for about 1 hour at ambient temperature and then the solution was allowed to stand at ambient temperature for 18 hours. This solution after standing for 18 hours had a thin layer chromatograph which showed two major products. The solvent was removed by vacuum leaving 6.28 grams of a beige solid. Two and five-tenths (2.5 grams) grams of this beige solid was dissolved in a small amount of methyl alcohol and adsorbed onto alumina, which was then packed on top of a 10 inch × 1 inch column of alumina (neutral, grade 3) and eluted with a solvent mixture of ethyl acetate and carbon tetrachloride having a volume ratio of 2 to 1. The first 100 milliliters of the eluant was discarded and the remaining eluant was collected and the eluant solvent was evaporated to yield 0.76 grams of 1-(3-methyl-5-isothiazolyl)-2-oxo-3-methyl-5-ethylhexahydro-1,3,5-triazine. Recrystallization of the triazine from 30 milliliters of a benzene/hexane solvent mixture having a volume ratio of 1 to 2 yielded 0.55 grams of 1-(3-methyl-5-isothiazolyl)-2-oxo-3-methyl-5-ethylhexahydro-1,3,5-triazine which had a melting point of 108° to 111° C. The overall yield of the reaction was 29 percent. The material had an infrared spectrum taken as a mull ($v_{mull}$ $^{max}$) showing maxima at the following frequencies: 1645, 1300, 790, 755, and 730 centimeters $^{-1}$. The nuclear magnetic resonance spectrum was taken in deuterochloroform [NMR ($CDCl_3$)] 1.15$\delta$ (singlet, 3H), 2.33$\delta$ (singlet, 3H), 2.84$\delta$ (quartet, 2H), 2.97$\delta$ (singlet, 3H), 4.31$\delta$ (singlet, 2H), 4.72$\delta$ (singlet, 2H), and 6.26$\delta$ (singlet, 1H).

EXAMPLE II

Synthesis of 1-(3-Methyl-5-isothiazolyl)-2-oxo-3-methyl-5-isopropylhexahydro-1,3,5-triazine The procedure given above for Example I was carried out using 4.4 grams (0.026 mole) of the 1-(3-methyl-5-isothiazolyl)-3-methylurea, 25 milliliters of dimethylformamide, 8 milliliters of 37 percent formaldehyde, and 3 milliliters of isopropylamine. After the reaction solution had stood for four days at ambient temperature, no products precipitated from the solution and therefore the solvent was removed by vacuum as mentioned in Example I. The solid remaining (6.5 grams) was stirred with three portions of 50 milliliters of ethyl ether, filtered and evaporated. This process was repeated three times (using a total volume of 450 milliliters of ether) which gave 2.05 grams of an ether-soluble material which contained the desired triazine. The 2.5 grams of ether-soluble material was absorbed onto alumina and eluted as described in Example I. The first 75 milliliters of eluant was discarded and the remaining eluant was collected in 20 milliliter fractions. The desired triazine was noted to be in fractions 4, 5, and 6 as indicated by thin layer chromatography and evaporation of the solvents from these fractions yielded 1.37 grams of the white solid of 1-(3-methyl-5-isothiazolyl)-2-oxo-3-methyl-5-isopropylhexahydro-1,3,5-triazine which had a melting point of 137° to 142° C. The overall reaction yield was 19 percent. It had $v_{mull}$ $^{max}$ of 1645, 1525, 1305, 795, 735 centimeters $^{-1}$; NMR ($CDCl_3$) 1.13$\delta$ (doublet, 6H, J = 6.0), 2.33$\delta$ (singlet, 3H), 2.94$\delta$ (singlet, 3H), 3.16$\delta$ (hept., 1H, J = 6.0), 4.37$\delta$ (singlet, 2H), 4.77$\delta$ (singlet, 2H), and 6.26$\delta$ (singlet, 1H).

EXAMPLE III

Synthesis of 1-(3-Methyl-5-isothiazolyl)-2-oxo-5-t-butyl-3-methyl-hexahydro-1,3,5-triazine The procedure given in Example I was followed and using the same amounts of the above-mentioned urea, but 50 milliliters of dimethylformamide, 8 milliliters of 37 percent aqueous formaldehyde, and 2.1 milliliters of t-butylamine. Because only a mild exotherm was noted (33° C.), the flask was heated on a steam bath for 30 minutes and then 0.5 milliliters more of t-butylamine was added and the flask was stoppered and allowed to stand for three days at ambient temperature. A crystalline solid formed in solution and filtration and washing with water gave 1.95 grams of material. Upon standing, crystals began forming in the filtrate so that the flask was chilled in an ice bath for a half hour. Filtration afforded 2.04 grams of a second batch of crystals. Thin layer chromatography of the first batch of crystals showed it to be the desired triazone contaminated by approximately 20 percent with the undesired 5-t-butyl-7-(N-methylcarbamoyl)-3-methylisothiazolyl[5,4-d]-4,5,6,7-tetrahydropyrimidine, which is a product caused by a side reaction, as indicated in reaction C. This mixture can be separated by column chromatography as described in Examples I and II.

EXAMPLE IV

The procedure of Example III was repeated but the reaction solution was allowed to stand two days and the solid which formed was removed by filtration, washed with water, and dried to yield 1.78 grams of 1-(3-methyl-5-isothiazolyl)-2-oxo-5-t-butyl-3-methylhexahydro-1,3,5-triazine which was pure as shown by thin layer chromatography. This product had a melting point of 198° to 201° C. and the overall yield was 22 percent. It had $v_{mull}^{max}$ of 2960, 1645, 1530, and 1310 centimeters$^{-1}$; NMR (CDCl$_3$) of 1.18$\delta$ (singlet, 9H), 2.37$\delta$ (singlet, 3H), 2.97$\delta$ (singlet, 3H), 4.43$\delta$ (singlet, 2H), 4.86$\delta$ (singlet, 2H), and 6.28$\delta$ (singlet, 1H).

UTILITY AND APPLICATION OF THE COMPOSITIONS a. Manner of Applications and Weeds Controlled

Undesirable plants (weeds), as used herein and in the Claims, are primarily broadleaf and grassy weed species, which are effectively controlled according to this invention by the use of the compositions of general formulas (I) and (II), usually by contacting the weeds with an effective amount, preferably a herbicidal amount of the compound. As used herein and in the Claims, the phrase "contacting a weed" means any manner in which one or more of the compositions described herein contact a weed described herein. This contact can be made by application of one or more of the compounds to the soil itself or to the weed (e.g., the weed environment) either prior to (preemergence) or after emergence of the weed (postemergence), or in any combination thereof, but the preferred method is to contact the weed after emergence of the weeds from the seeds (postemergence), especially when the weeds are only 1 to 2 weeks old and are rapidly growing. If both crop plants and weeds are emerging, then the compound is applied after emergence of both. A preferred method is to contact the foliage of the weed with an effective amount of one or more of the compositions described herein. This may be readily achieved by applying the composition itself, but preferably it is applied in the form of a suitable agricultural composition to the foliage of the weed. The phrase "effective amount to control said weed", as used herein and in the Claims, means that amount required to retard the normal growth of the weed. Preferably, a lethal herbicidal dosage will be used. A workable lethal dosage for plant contact is from 0.25 to 500 pounds per acre (0.27 to 550 kilograms/hectare) of one or more of the compositions described, whether applied by itself or in the form of an agricultural composition, while from 0.25 to 250 pounds per acre (0.27 to 250 kilograms/hectare) is generally the range to use, normally from 0.25 to 50 pounds per acre (0.27 to 55 kilograms/hectare), but preferably from 0.25 to 10 pounds per acre (0.27 to 11 kilograms/hectare) under optimum conditions.

It has been discovered that the compositions of general formulas (I) and (II), such as 1-(3-methyl-5-isothiazolyl)-2-oxo-3-methyl-5-ethylhexahydro-1,3,5-triazine, are particularly effective against weeds, such as broadleaf weeds and grassy weeds, but particularly against broadleaf weeds. The compositions are effective particularly against weeds of the genera: *Brassica, Echinochloa, Abutilon, Datura, Ipomoea, Sesbania, Xanthium,* and *Gossypium* and their equivalents. The compounds were found extremely effective against the species: *Brassica kaber*, D.C. (wild mustard), *Echinochloa crusgalli* (barnyardgrass), *Datura stramonium* (jimsonweed), *Ipomoea spp.* (morningglory), *Abutilon theophrasti* (velvetleaf), *Sesbania spp.* (coffeeweed), *Xanthium pensylvanicum* (common cocklebur), and *Gossypium hirsutum* (cotton).

The following example illustrates a manner in which this invention may be practiced.

The mixture of weed seeds was a representative cross-section of broadleaf and grassy weeds, and contained seeds from species of each of the following genera: *Brassica, Echinochloa, Abutilon, Datura, Ipomoea, Sesbania, Xanthium,* and *Gossypium.* The particular weed species were: *Brassica kaber*, D.C. (wild mustard), *Echinochloa crusgalli* L. Beauv. (barnyardgrass), *Datura stramonium* (jimsonweed), *Ipomoea spp.* (morningglory), *Abutilon theophrasti* (velvetleaf), *Sesbania spp.* (coffeeweed), *Xanthium pensylvanicum* (common cocklebur), and *Gossypium hirsutum* (L.) Coker variety (cotton).

PROCEDURE

Screened top soil which had been limed to a pH of 6.5 and had been fertilized with 12-12-12 farm grade fertilizer at a rate of about (75) pounds per acre of total nitrogen, was placed in plastic (2.75) inch square pots to a depth of about (2.5) inches. Single weed species were grown per pot, by placing the seeds of a single weed species on top of the soil in the pot, and covering them with (0.25) inch of soil. The number of seeds of a weed species per pot varied from about (8) to (40) depending upon the particular weed species grown in the pots. The weed species were planted according to a growth cycle to insure that at the time of postemergence testing of the compounds, that the weed plant emerging had at least one true leaf, e.g., cocklebur was planted prior to grasses, such as barnyardgrass. The pots after being seeded were watered and placed in the laboratory growth room where the weeds were grown under artificial light from Gro-Lux ® fluorescent lights at a temperature of about 23°–33° C. and a relative humidity of 50 to 80 percent, until the emerging plants had several true leaves.

The test compound was dissolved in a standard solvent mixture of acetone, methanol, dimethylformamide (90:8:2 volume/volume) and was applied postemergence to the leaves at the rate of 482 milligrams of the test compound per 4.63 square feet which is equivalent to 10 pounds of active ingredient per surface acre (10 lbs. ai/acre), by means of a herbicidal sprayer. The sprayer was equipped with a Tee-Jet 8001 spray nozzle tip and the sprayer operated in the range of 35–40 pounds per square inch pressure with compressed air. The sprayer was set to deliver (50) gallons of solution per surface acre.

The potted plants, which had at least one true leaf, were placed on a tray, and the tray was placed on a conveyor belt which passed through the sprayer at about (0.9) foot per second. The tray tripped a microswitch which activated a solenoid valve to release the spray solution containing the test compound.

Immediately after the spray treatment, the sprayed pots of weeds were transferred to the above mentioned growth room and held there for visual observations of the weeds. Daily observations were made for interim changes in the weeds and a final observation was made (14) days after the postemergence spray treatment. This final observation included abnormal physiological changes, such as: stem bending, petiole curvature, epinasty, hyponasty, retardation, stimulation, root development, necrosis, and retarded growth regulant characteristics.

These observations were reported as Injury Ratings based on a relative scale of (0) to (10); (0) meaning no observed injury or control, and (10) meaning severe injury resulting in complete control, all plants were killed. The abnormal physiological ratings were reported as necrosis (Ne), chlorosis (Cl), retardation (R), and no visual abnormal responses, zero (0).

EXAMPLE V

When 1-(3-methyl-5-isothiazolyl)-2-oxo-3-methyl-5-ethylhexahydro-1,3,5-triazine from Example I was applied postemergence at 10 pounds of active ingredient per acre (1.1 kilogram/hectare) according to the procedure described above, the following results shown in Table I were obtained.

Column 1 of Table I gives the weed species, both its scientific and common name, and Column 2 gives the control rating and the physiological response obtained.

TABLE I

Postemergence Control At 10 Pounds Of Active Ingredient/Acre of 1-(3-Methyl-5-Isothiazolyl)-2-Oxo-3-Methyl-5-Ethylhexahydro-1,3,5-Triazine

| Weed Species | Control Rating | Abnormal Response |
|---|---|---|
| Xanthium pensylvanicum (L.) common cocklebur | 10 | Necrosis |
| Datura stramonium (L.) jimsonweed | 10 | Necrosis |
| Brassica kaber (D.C.) wild mustard | 10 | Necrosis |
| Gossypium hirsutum (L.) (Coker variety) cotton | 10 | Necrosis |
| Sesbania spp. coffeeweed | 9 | Necrosis |
| Abutilon theophrasti (L.) velvetleaf | 10* | Necrosis |
| Ipomoea spp. morningglory | 10 | Necrosis |
| Echinochloa crusgalli (L.) Beauv. barnyardgrass | 7 | Necrosis, Retardation |
| Avena fatua wild oats | 10* | Necrosis |

*21 day rating

EXAMPLE VI

When 1-(3-methyl-5-isothiazolyl)-2-oxo-3-methyl-5-isopropylhexahydro-1,3,5-triazine from Example II was applied postemergence at 10 pounds of active ingredient per acre (11 kilograms/hectare) according to the procedure described above, the following results shown in Table II were obtained.

Column 1 of Table II gives the weed species, both its scientific and common name, and Column 2 gives the control rating and the physiological response obtained.

TABLE II

Postemergence Control at 10 Pounds of Active Ingredient/Acre of 1-(3-Methyl-5-Isothiazolyl)-2-Oxo-3-Methyl-5-Isopropylhexahydro-1,3,5-triazine

| Weed Species | Control Rating | Abnormal Response |
|---|---|---|
| Xanthium pensylvanicum (L.) common cocklebur | 10 | Necrosis |
| Datura stramonium (L.) jimsonweed | 10 | Necrosis |
| Brassica kaber (D.C.) wild mustard | 10 | Necrosis |
| Gossypium hirsutum (L.) (Coker variety) cotton | 10 | Necrosis |
| Sesbania spp. coffeeweed | 9 | Necrosis (regrowth occurring) |
| Abutilon theophrasti (L.) velvetleaf | 10 | Necrosis |
| Ipomoea spp. morningglory | 10 | Necrosis |
| Echinochloa crusgalli (L.) Beauv. barnyardgrass | 8 | Necrosis, Retardation |
| Avena fatua wild oats | 10 | Necrosis |

These test results illustrate the herbicidal activity against weeds of the compositions of general formulas (I) and (II), and in particular, broadleaf weeds. Although the lethal dosage or herbicidally effective amount shown was for 10 pounds per acre (11 kilograms/hectare), such a dosage can be varied from 0.25 to 200 pounds per acre (0.27 to 220 kilograms/hectare), depending upon the species, growth stage, and the weather, but generally 0.25 to 50 pounds per acre will suffice, and under optimum conditions 0.25 to 10 pounds per acre is preferred.

b. Use of Formulations

Although the plants may be contacted with the compositions of general formulas (I) and (II), such as 1-(3-methyl-5-isothiazolyl)-2-oxo-3-methyl-5-isopropylhexahydro-1,3,5-triazine itself or with the other compounds disclosed herein, as directly synthesized or as granules, it is preferable to use other suitable agricultural formulations which contain other ingredients which enhance application of the compound or compounds. These agricultural formulations will generally comprise from 5 to 95 percent by weight of the triazine mentioned herein singularly or as a mixture of the compounds of the general formulas. The mixture may include a trace of each of the other compounds mentioned herein or a substantial amount. The other ingredients of these formulations will be from 1 to 95 percent by weight of an agricultural diluent, or from 1 to 20 percent by weight of a surface active agent or other ingredients required to produce wettable powders, dusts, solutions, emulsifiable concentrates, granules, and the like.

Granules will contain from 5 percent to 25 percent active ingredient extended upon a granular base. When the toxicant compounds are solids, they may be dissolved in one or more solvents and then sprayed upon the absorptive carriers, such as attapulgite clay, synthetic fine silica, and synthetic calcium and sodium alumino-silicates. In some cases the solvent or solvents may later be evaporated off. Granules produced by extrusion or tumbling will contain like amounts of active ingredients.

Dusts are mixtures of the active compound with finely divided solids such as, talc, attapulgite clay, kieselguhr, and other organic and inorganic solids which act as diluents and carriers for the compound. The finely divided solids have an average particle size of less than 50 microns. A typical dust formulation will contain from 1.0 to 10.0 parts by weight of one of the triazines mentioned herein or in mixture with the other compounds of general formulas (I) and (II) from 99.0 to 90.0 parts by weight of talc.

Wettable powders for preemergent or postemergent application are finely divided solid particles, which disperse readily in water or other liquids. The wettable powder is applied to the soil, seed, or plant as a dry dust or as a water or other liquid emulsion.

Typical wettable powder carriers are Fuller's earth, Kaolin clays, silicas, and other highly absorbent, readily wettable, inorganic diluents. Wettable powders normally contain about 5 to 80 weight percent of the active ingredient, depending on the absorbency of the carrier, and usually contain a small amount of a wetting, dispersing, or emulsifying agent to facilitate dispersion.

For example, a useful wettable powder formulation comprises by weight about 80.8 parts of one or more of the compounds of general formulas (I) and (II), 1719 parts of Palmetho clay, and 1.0 parts of sodium lignosulfate and 0.3 parts of sulfonated aliphatic polyester as wetting agents.

Other postemergent formulations are emulsifiable concentrates. These are homogeneous liquid or paste compositions which are dispersible in water or other liquids. They may consist entirely of one or more of the compounds of general formulas (I) and (II) and a liquid or solid emulsifying agent, or they may also contain a liquid solvent, such as xylene, heavy aromatic naphthas, or other non-volatile organic solvents. These emulsifiable concentrates are dispersed in a liquid carrier, e.g., water, and generally are applied as a spray to the area or plant to be treated. The weight percent of the compounds of general formulas (I) and (II) in these concentrates varies with the manner of application, but generally is from 0.5 to 95 percent.

Representative wetting, dispersing, and emulsifying agents for the agricultural formulations are alkyl and alkylaryl sulfonates and sulfates, and their alkali salts; polyethylene oxides, sulfoxided oils, fatty acid esters of polyhydric alcohols, and other surface-active agents, e.g., TWEEN 20 ®, a commercial surfactant. If used, the surfactant would vary from 0.25 to 15 weight percent of the composition.

Other formulations for herbicidal applications include simple solutions of the compound in solvents in which it is completely soluble at the desired concentration, e.g., acetone or other organic solvents; aerial spray formulations comprising relatively coarse particles coated with the compounds of general formulas (I) and (II), and pressurized spray formulations such as aerosols, which use low boiling dispersant solvents such as Freon. All of these formulations may be used to apply the active compound to the area to be treated.

These formulations may also include other agriculturally useful materials such as pesticides and herbicides which are non-toxic to the desired vegetation, but which are effective against other weeds, insects, microorganisms, and nematodes, so that one application will serve to rid the area of several undesirable species. For example, the triazines mentioned herein, such as 1-(3-methyl-5-isothiazolyl)-2-oxo-3-methyl-5-ethylhexahydro-1,3,5-triazine may be used with non-basic materials in formulations which contain ureas, thiocarbamates, carbamates, which increase the useful herbicidal spectrum of the thiazole, reduce the number of applications required by farmers and others who require use of these compounds to assist the healthful growth of crops.

c. Effective Amounts to Apply

Normally the effective amount of the compound to apply will vary with the environmental and climatic conditions.

When one or more of the compounds of the general formulas (I) and (II) are applied in the form of a suitable agricultural composition, the application rate of such formulation is such that the herbicidal dosage of a composition of the general formulas (I) or (II) itself, or a mixture of the compositions, is between 0.25 to 500 pounds per acre (0.27 to 550 kilograms/hectare). Generally, the rate is from 0.25 to 50 pounds per acre (0.27 to 55 kilograms/hectare), normally from 0.25 to 20 pounds per acre, but preferably from 1 to 10 pounds per acre (1.1 to 11 kilograms/hectare) under optimum conditions. The preferred compositions mentioned herein are used at the lower rate.

Generally, the compounds 1-(3-methyl-5-isothiazolyl)-2-oxo-3-methyl-5-ethylhexahydro-1,3,5-triazine, 1-(3-ethyl-4-methyl-5-isothiazolyl)-2-oxo-3-methyl-5-ethylhexahydro-1,3,5-triazine, 1-(4-ethyl-5-n-propyl-5-isothiazolyl)-2-oxo-3-methyl-5-ethylhexahydro-1,3,5-triazine, and 1-(3-benzyl-4-phenyl-5-isothiazolyl)-2-oxo-3-methyl-5-ethylhexahydro-1,3,5-triazine are used at lower rates of about 50 pounds of the active ingredient per acre to 1 pound of the active ingredient per acre.

While the invention has been described with reference to specific details of certain illustrative embodiments, it is not intended that it shall be limited thereby except insofar as such details appear in the accompanying claims.

We claim:
1. A composition of the formula:

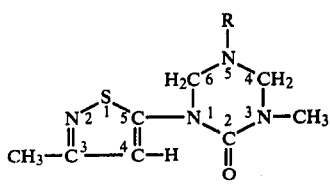

wherein:
R is a lower alkyl of from two to four carbon atoms, a lower alkenyl of from three to five carbon atoms with a saturated carbon atom attached to the nitrogen atom, or a lower alkynyl of from three to five carbon atoms with a saturated carbon atom attached to the nitrogen atom.

2. The composition as recited in claim 1, wherein R is a lower alkyl of from 2 to 4 carbon atoms.

3. The composition 1-(3-methyl-5-isothiazolyl)-2-oxo-3-methyl-5-ethylhexahydro-1,3,5-triazine.

4. A composition of 1-(3-methyl-5-isothiazolyl)-2-oxo-3-methyl-5-n-propylhexahydro-1,3,5-triazine.

5. A composition of 1-(3-methyl-5-isothiazolyl)-2-oxo-3-methyl-5-isopropylhexahydro-1,3,5-triazine.

6. A composition 1-(3-methyl-5-isothiazolyl)-2-oxo-3-methyl-5-t-butylhexahydro-1,3,5-triazine.

7. The composition as recited in claim 2, wherein R is a lower alkenyl of from three to five carbon atoms with a saturated carbon atom attached to the nitrogen atom.

8. The composition as recited in claim 1, wherein R is an alkenyl selected from the group consisting of allyl, 2-butenyl, 3-butenyl, or 2-methyl-2-propenyl.

9. The composition 1-(3-methyl-5-isothiazolyl)-2-oxo-3-methyl-5-allylhexahydro-1,3,5-triazine.

10. The composition 1-(3-methyl-5-isothiazolyl)-2-oxo-3-methyl-5-(2-methyl-2-propenyl)hexahydro-1,3,5-triazine.

11. The composition as recited in claim 1, wherein R is a lower alkynyl of from three to five carbon atoms with a saturated carbon atom attached to the nitrogen atom.

12. The composition of claim 1, wherein R is an alkynyl selected from the group consisting of 2-propynyl, 1,1-dimethyl-2-propynyl, 2-butynyl, and 3-butynyl.

13. The composition 1-(3-methyl-5-isothiazolyl)-2-oxo-3-methyl-5-(2-propynyl)hexahydro-1,3,5-triazine.

14. The composition 1-(3-methyl-5-isothiazolyl)-2-oxo-3-methyl-5-(1,1-dimethyl-2-propynyl)hexahydro-1,3,5-triazine.

15. A composition of the formula:

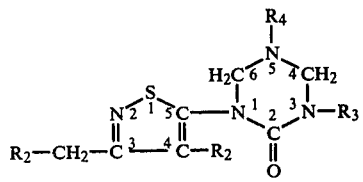

wherein:
$R_2$ is methyl, ethyl, n-propyl, phenyl, p-chlorophenyl, or p-nitrophenyl;
$R_3$ is a lower alkyl of from one to four carbon atoms, or a lower alkenyl of from three to five carbon atoms with a saturated carbon atom attached to the nitrogen atom, or a lower alkynyl of from three to five carbon atoms with a saturated carbon atom attached to the nitrogen atom; and $R_4$ is a lower alkyl of from one to four carbon atoms, or a lower alkenyl of from three to five carbon atoms with a saturated carbon atom attached to the nitrogen atom, or a lower alkynyl of from three to five carbon atoms with a saturated carbon atom attached to the nitrogen atom; but both $R_3$ and $R_4$ cannot be methyl.

16. The composition as recited in claim 15, wherein $R_2$ is methyl.

17. The composition as recited in claim 16, wherein $R_3$ is a lower alkyl selected from the group consisting of methyl, isopropyl, or t-butyl.

18. The composition as recited in claim 17, wherein $R_4$ is a lower alkyl selected from the group consisting of methyl, ethyl, isopropyl, or t-butyl.

19. The composition as recited in claim 17, wherein $R_4$ is a lower alkenyl of from three to five carbon atoms with a saturated carbon atom attached to the nitrogen atom.

20. The composition as recited in claim 17, wherein $R_4$ is a lower alkenyl selected from the group consisting of allyl, 2-butenyl, 3-butenyl, or 2-methyl-2-propenyl.

21. The composition as recited in claim 17, wherein $R_4$ is a lower alkynyl of from three to five carbon atoms with a saturated carbon atom attached to the nitrogen atom.

22. The composition as recited in claim 17, wherein $R_4$ is a lower alkynyl selected from the group consisting of 2-propynyl, 2-butynyl, 3-butynyl, or 1,1-dimethyl-2-propynyl.

23. The composition as recited in claim 16, wherein $R_3$ is methyl.

24. A composition of 1-(3-ethyl-4-methyl-5-isothiazolyl)-2-oxo-3-methyl-5-ethylhexahydro-1,3,5-triazine.

25. A composition of 1-(3-ethyl-4-methyl-5-isothiazolyl)-2-oxo-3-methyl-5-isopropylhexahydro-1,3,5-triazine.

26. A composition of 1-(3-ethyl-4-methyl-5-isothiazolyl)-2-oxo-3-methyl-5-t-butylhexahydro-1,3,5-triazine.

27. The composition as recited in claim 23, wherein $R_4$ is a lower alkenyl or from three to five carbon atoms with a saturated carbon atom attached to the nitrogen atom.

28. The composition as recited in claim 23, wherein $R_4$ is a lower alkenyl selected from the group consisting of allyl, 2-butenyl, 3-butenyl, or 2-methyl-2-propenyl.

29. A composition of 1-(3-ethyl-4-methyl-5-isothiazolyl)-2-oxo-3-methyl-5-allylhexahydro-1,3,5-triazine.

30. A composition of 1-(3-ethyl-4-methyl-5-isothiazolyl)-2-oxo-3-methyl-5-(2-methyl-2-propenyl)hexahydro-1,3,5-triazine.

31. The composition as recited in claim 23, wherein $R_4$ is a lower alkynyl of from three to five carbon atoms with a saturated carbon atom attached to the nitrogen atom.

32. The composition as recited in claim 23, wherein $R_4$ is a lower alkynyl selected from the group consisting of 2-propynyl, 2-butynyl, 3-butynyl, or 1,1-dimethyl-2-propynyl.

33. A composition of 1-(3-ethyl-4-methyl-5-isothiazolyl)-2-oxo-3-methyl-5-(2-propynyl)hexahydro-1,3,5-triazine.

34. A composition of 1-(3-ethyl-4-methyl-5-isothiazolyl)-2-oxo-3-methyl-5-(1,1-dimethyl-2-propynyl)hexahydro-1,3,5-triazine.

35. The composition as recited in claim 16, wherein $R_3$ is a lower alkenyl of from three to five carbon atoms with a saturated carbon atom attached to the nitrogen atom.

36. The composition as recited in claim 16, wherein $R_3$ is a lower alkenyl selected from the group consisting of allyl, 2-butenyl, 3-butenyl, or 2-methyl-2-propenyl.

37. The composition as recited in claim 36, wherein $R_4$ is a lower alkyl of from one to four carbon atoms.

38. The composition as recited in claim 36, wherein $R_4$ is a lower alkyl selected from the group consisting of methyl, ethyl, isopropyl, or t-butyl.

39. A composition of 1-(3-ethyl-4-methyl-5-isothiazolyl)-2-oxo-3-allyl-5-methylhexahydro-1,3,5-triazine.

40. A composition of 1-(3-ethyl-4-methyl-5-isothiazolyl)-2-oxo-3-allyl-5-ethylhexahydro-1,3,5-triazine.

41. A composition of 1-(3-ethyl-4-methyl-5-isothiazolyl)-2-oxo-3-allyl-5-isopropylhexahydro-1,3,5-triazine.

42. A composition of 1-(3-ethyl-4-methyl-5-isothiazolyl)-2-oxo-3-allyl-5-(t-butyl)hexahydro-1,3,5-triazine.

43. A composition of 1-(3-ethyl-4-methyl-5-isothiazolyl)-2-oxo-3-(2-methyl-2-propenyl)-5-methylhexahydro-1,3,5-triazine.

44. A composition of 1-(3-ethyl-4-methyl-5-isothiazolyl)-2-oxo-3-(2-methyl-2-propenyl)-5-ethylhexahydro-1,3,5-triazine.

45. A composition of 1-(3-ethyl-4-methyl-5-isothiazolyl)-2-oxo-3-(2-methyl-2-propenyl)-5-isopropylhexahydro-1,3,5-triazine.

46. A composition of 1-(3-ethyl-4-methyl-5-isothiazolyl)-2-oxo-3-(2-methyl-2-propenyl)-5-t-butylhexahydro-1,3,5-triazine.

47. The composition as recited in claim 36, wherein $R_4$ is a lower alkenyl of from three to five carbon atoms with a saturated carbon atom attached to the nitrogen atom.

48. The composition as recited in claim 36, wherein $R_4$ is a lower alkenyl selected from the group consisting of allyl, 2-butenyl, 3-butenyl, or 2-methyl-2-propenyl.

49. A composition of 1-(3-ethyl-4-methyl-5-isothiazolyl)-2-oxo-3,5-diallylhexahydro-1,3,5-triazine.

50. A composition of 1-(3-ethyl-4-methyl-5-isothiazolyl)-2-oxo-3-allyl-5-(2-methyl-2-propenyl)hexahydro-1,3,5-triazine.

51. A composition of 1-(3-ethyl-4-methyl-5-isothiazolyl)-2-oxo-3,5-bis-(2-methyl-2-propenyl)hexahydro-1,3,5-triazine.

52. A composition of 1-(3-ethyl-4-methyl-5-isothiazolyl)-2-oxo-3-(2-methyl-2-propenyl)-5-allkylhexahydro-1,3,5-triazine.

53. The composition as recited in claim 36, wherein $R_4$ is a lower alkynyl of from three to five carbon atoms with a saturated carbon atom attached to the nitrogen atom.

54. The composition as recited in claim 36, wherein $R_4$ is a lower alkynyl selected from the group consisting of 2-propynyl, 2-butynyl, 3-butynyl, or 1,1-dimethyl-2-propynyl.

55. A composition of 1-(3-ethyl-4-methyl-5-isothiazolyl)-2-oxo-3-allyl-5-(2-propynyl)hexahydro-1,3,5-triazine.

56. A composition of 1-(3-ethyl-4-methyl-5-isothiazolyl)-2-oxo-3-allyl-5-(1,1-dimethyl-2-propynyl)-hexahydro-1,3,5-triazine.

57. A composition of 1-(3-ethyl-4-methyl-5-isothiazolyl)-2-oxo-3-(2-methyl-2-propenyl)-5-(2-propynyl)hexahydro-1,3,5-triazine.

58. A composition of 1-(3-ethyl-4-methyl-5-isothiazolyl)-2-oxo-3-(2-methyl-2-propenyl)-5-(1,1-dimethyl-2-propynyl)hexahydro-1,3,5-triazine.

59. The composition as recited in claim 16, wherein $R_3$ is a lower alkynyl of from three to five carbon atoms with a saturated carbon atom attached to the nitrogen atom.

60. The composition as recited in claim 16, wherein $R_3$ is a lower alkynyl selected from the group consisting of 2-propynyl, 2-butynyl, 3-butynyl, or 1,1-dimethyl-2-propynyl.

61. The composition as recited in claim 60, wherein $R_4$ is a lower alkyl of from one to four carbon atoms.

62. The composition as recited in claim 60, wherein $R_4$ is a lower alkyl selected from the group consisting of methyl, ethyl, isopropyl, or t-butyl.

63. A composition of 1-(3-ethyl-4-methyl-5-isothiazolyl)-2-oxo-3-(2-propynyl)-5-methylhexahydro-1,3,5-triazine.

64. A composition of 1-(3-ethyl-4-methyl-5-isothiazolyl)-2-oxo-3-(2-propynyl)-5-ethylhexahydro-1,3,5-triazine.

65. A composition of 1-(3-ethyl-4-methyl-5-isothiazolyl)-2-oxo-3-(2-propynyl)-5-isopropylhexahydro-1,3,5-triazine.

66. A composition of 1-(3-ethyl-4-methyl-5-isothiazolyl)-2-oxo-3-(2-propynyl)-5-t-butylhexahydro-1,3,5-triazine.

67. A composition of 1-(3-ethyl-4-methyl-5-isothiazolyl)-2-oxo-3-(1,1-dimethyl-2-propynyl)-5-methylhexahydro-1,3,5-triazine.

68. A composition of 1-(3-ethyl-4-methyl-5-isothiazolyl)-2-oxo-3-(1,1-dimethyl-2-propynyl)-5-ethylhexahydro-1,3,5-triazine.

69. A composition of 1-(3-ethyl-4-methyl-5-isothiazolyl)-2-oxo-3-(1,1-dimethyl-2-propynyl)-5-isopropylhexahydro-1,3,5-triazine.

70. A composition of 1-(3-ethyl-4-methyl-5-isothiazolyl)-2-oxo-3-(1,1-dimethyl-2-propynyl)-5-t-butylhexahydro-1,3,5-triazine.

71. The composition as recited in claim 59, wherein $R_4$ is a lower alkenyl of from three to five carbon atoms with a saturated carbon atom attached to the nitrogen atom.

72. The composition as recited in claim 60, wherein $R_4$ is a lower alkenyl of from three to five carbon atoms with a saturated carbon atom attached to the nitrogen atom.

73. The composition as recited in claim 60, wherein $R_4$ is a lower alkenyl selected from the group consisting of allyl, 2-butenyl, 3-butenyl, or 2-methyl-2-propenyl.

74. A composition of 1-(3-ethyl-4-methyl-5-isothiazolyl)-2-oxo-3-(2-propynyl)-5-allylhexahydro-1,3,5-triazine.

75. A composition of 1-(3-ethyl-4-methyl-5-isothiazolyl)-2-oxo-3-(2-propynyl)-5-(2-methyl-2-propenyl)hexahydro-1,3,5-triazine.

76. A composition of 1-(3-ethyl-4-methyl-5-isothiazolyl)-2-oxo-3-(1,1-dimethyl-2-propynyl)-5-allylhexahydro-1,3,5-triazine.

77. A composition of 1-(3-ethyl-4-methyl-5-isothiazolyl)-2-oxo-3-(1,1-dimethyl-2-propynyl)-5-(2-methyl-2-propenyl)hexahydro-1,3,5-triazine.

78. The composition as recited in claim 59, wherein $R_4$ is a lower alkynyl of from three to five carbon atoms with a saturated carbon atom attached to the nitrogen atom.

79. The composition as recited in claim 59, wherein $R_4$ is a lower alkynyl selected from the group consisting of 2-propynyl, 2-butynyl, 3-butynyl, or 1,1-dimethyl-2-propynyl.

80. The composition as recited in claim 59, wherein $R_4$ is 2-propynyl.

81. The composition as recited in claim 59, wherein $R_4$ is 1,1-dimethyl-2-propynyl.

82. The composition as recited in claim 60, wherein $R_4$ is a lower alkynyl of from three to five carbon atoms with a saturated carbon atom attached to the nitrogen atom.

83. The composition as recited in claim 60, wherein $R_4$ is a lower alkynyl selected from the group consisting of 2-propynyl, 2-butynyl, 3-butynyl, or 1,1-dimethyl-2-propynyl.

84. The composition as recited in claim 60, wherein $R_4$ is 2-propynyl.

85. The composition as recited in claim 60, wherein $R_4$ is 1,1-dimethyl-2-propynyl.

86. A composition of 1-(3-ethyl-4-methyl-5-isothiazolyl)-2-oxo-3,5-bis-(2-propynyl)hexahydro-1,3,5-triazine.

87. A composition of 1-(3-ethyl-4-methyl-5-isothiazolyl)-2-oxo-3-(2-propynyl)-5-(1,1-dimethyl-2-propynyl)hexahydro-1,3,5-triazine.

88. A composition of 1-(3-ethyl-4-methyl-5-isothiazolyl)-2-oxo-3-(1,1-dimethyl-2-propynyl)-5-(2-propynyl)hexahydro-1,3,5-triazine.

89. A composition of 1-(3-ethyl-4-methyl-5-isothiazolyl)-2-oxo-3,5-bis-(1,1-dimethyl-2-propynyl)hexahydro-1,3,5-triazine.

90. The composition as recited in claim 15, wherein $R_2$ is ethyl.

91. The composition as recited in claim 90, wherein $R_3$ is methyl.

92. The composition as recited in claim 91, wherein $R_4$ is a lower alkyl selected from the group consisting of isopropyl or t-butyl.

93. The composition as recited in claim 91, wherein $R_4$ is a lower alkenyl selected from the group consisting of allyl, 2-methyl-2-propenyl, 2-butenyl, and 3-butenyl.

94. The composition as recited in claim 91, wherein $R_4$ is a lower alkynyl selected from the group consisting of 2-propynyl, 1,1-dimethyl-2-propynyl, 2-butynyl, and 3-butynyl.

95. A composition of 1-(3-n-propyl-4-ethyl-5-isothiazolyl)-2-oxo-3-methyl-5-allylhexahydro-1,3,5-triazine.

96. A composition of 1-(3-n-propyl-4-ethyl-5-isothiazolyl)-2-oxo-3-methyl-5-(2-methyl-2-propenyl)hexahydro-1,3,5-triazine.

97. A composition of 1-(3-n-propyl-4-ethyl-5-isothiazolyl)-2-oxo-3-methyl-5-(2-propynyl)hexahydro-1,3,5-triazine.

98. A composition of 1-(3-n-propyl-4-ethyl-5-isothiazolyl)-2-oxo-3-methyl-5-(1,1-dimethyl-2-propynyl)-hexahydro-1,3,5-triazine.

99. The composition as recited in claim 90, wherein $R_3$ is a lower alkenyl selected from the group consisting of allyl or 2-methyl-2-propenyl.

100. The composition as recited in claim 99, wherein $R_4$ is a lower alkyl selected from the group consisting of methyl, isopropyl, or t-butyl.

101. The composition as recited in claim 99, wherein $R_4$ is a lower alkenyl selected from the group consisting of allyl or 2-methyl-2-propenyl.

102. The composition as recited in claim 99, wherein $R_4$ is a lower alkynyl selected from the group consisting of 2-propynyl or 1,1-dimethyl-2-propynyl.

103. The composition as recited in claim 90, wherein $R_3$ is a lower alkynyl selected from the group consisting of 2-propynyl or 1,1-dimethyl-2-propynyl.

104. The composition as recited in claim 103, wherein $R_4$ is a lower alkyl selected from the group consisting of methyl, isopropyl, or t-butyl.

105. The composition as recited in claim 103, wherein $R_4$ is a lower alkenyl selected from the group consisting of allyl or 2-methyl-2-propenyl.

106. The composition as recited in claim 103, wherein $R_4$ is a lower alkynyl selected from the group consisting of 2-propynyl or 1,1-dimethyl-2-propynyl.

107. The composition as recited in claim 15, wherein $R_2$ is p-chlorophenyl.

108. The composition as recited in claim 107, wherein $R_3$ is methyl.

109. The composition as recited in claim 108, wherein $R_4$ is a lower alkyl selected from the group consisting of isopropyl or t-butyl.

110. The composition as recited in claim 109, wherein $R_4$ is a lower alkenyl selected from the group consisting of allyl or 2-methyl-2-propenyl.

111. The composition as recited in claim 109, wherein $R_4$ is a lower alkynyl selected from the group consisting of 2-propynyl or 1,1-dimethyl-2-propynyl.

112. The composition as recited in claim 108, wherein $R_3$ is a lower alkenyl selected from the group consisting of allyl or 2-methyl-2-propenyl.

113. The composition as recited in claim 112, wherein $R_4$ is a lower alkyl selected from the group consisting of methyl, isopropyl, or t-butyl.

114. The composition as recited in claim 112, wherein $R_4$ is a lower alkenyl selected from the group consisting of allyl or 2-methyl-2-propenyl.

115. The composition as recited in claim 112, wherein $R_4$ is a lower alkynyl selected from the group consisting of 2-propynyl or 1,1-dimethyl-2-propynyl.

116. The composition as recited in claim 107, wherein $R_3$ is a lower alkynyl selected from the group consisting of 2-propynyl or 1,1-dimethyl-2-propynyl.

117. The composition as recited in claim 116, wherein $R_4$ is a lower alkyl selected from the group consisting of methyl, isopropyl, or t-butyl.

118. The composition as recited in claim 116, wherein $R_4$ is a lower alkenyl selected from the group consisting of allyl or 2-methyl-2-propenyl.

119. The composition as recited in claim 116, wherein $R_4$ is a lower alkynyl selected from the group consisting of 2-propynyl or 1,1-dimethyl-2-propynyl.

120. The composition as recited in claim 15, wherein $R_2$ is p-nitrophenyl.

121. The composition as recited in claim 120, wherein $R_3$ is methyl.

122. The composition as recited in claim 121, wherein $R_4$ is a lower alkyl selected from the group consisting of isopropyl or t-butyl.

123. The composition as recited in claim 121, wherein $R_4$ is a lower alkenyl selected from the group consisting of allyl or 2-methyl-2-propenyl.

124. The composition as recited in claim 121, wherein $R_4$ is a lower alkynyl selected from the group consisting of 2-propynyl or 1,1-dimethyl-2-propynyl.

125. The composition as recited in claim 120, wherein $R_3$ is a lower alkenyl selected from the group consisting of allyl or 2-methyl-2-propenyl.

126. The composition as recited in claim 125, wherein $R_4$ is a lower alkyl selected from the group consisting of methyl, isopropyl, or t-butyl.

127. The composition as recited in claim 125, wherein $R_4$ is a lower alkenyl selected from the group consisting of allyl or 2-methyl-2-propenyl.

128. The composition as recited in claim 125, wherein $R_4$ is a lower alkynyl selected from the group consisting of 2-propynyl or 1,1-dimethyl-2-propynyl.

129. The composition as recited in claim 120, wherein $R_3$ is a lower alkynyl selected from the group consisting of 2-propynyl or 1,1-dimethyl-2-propynyl.

130. The composition as recited in claim 129, wherein $R_4$ is a lower alkyl selected from the group consisting of methyl, isopropyl, or t-butyl.

131. The composition as recited in claim 129, wherein $R_4$ is a lower alkenyl selected from the group consisting of allyl or 2-methyl-2-propenyl.

132. The composition as recited in claim 131, wherein $R_4$ is a lower alkynyl selected from the group consisting of 2-propynyl or 1,1-dimethyl-2-propynyl.

* * * * *

UNITED STATES PATENT AND TRADEMARK OFFICE
CERTIFICATE OF CORRECTION

PATENT NO. : 4,150,226
DATED : April 17, 1979
INVENTOR(S) : Hardies et al

It is certified that error appears in the above-identified patent and that said Letters Patent are hereby corrected as shown below:

Column 24, line 43, "or" should be --of--.

Signed and Sealed this

Eighteenth Day of March 1980

[SEAL]

Attest:

SIDNEY A. DIAMOND

Attesting Officer     Commissioner of Patents and Trademarks